US007238775B2

(12) United States Patent
Rivier et al.

(10) Patent No.: US 7,238,775 B2
(45) Date of Patent: Jul. 3, 2007

(54) RECEPTOR(SSTR4)-SELECTIVE SOMATOSTATIN ANALOGS

(75) Inventors: Jean E. F. Rivier, La Jolla, CA (US); Jean Claude Reubi, Berne (CH); Judit Erchegyi, San Diego, CA (US); Roland Riek, La Jolla, CA (US)

(73) Assignee: The Salk Institute for Biological Studies, San Diego, CA (US)

( * ) Notice: Subject to any disclaimer, the term of this patent is extended or adjusted under 35 U.S.C. 154(b) by 0 days.

(21) Appl. No.: 11/041,676

(22) Filed: Jan. 24, 2005

(65) Prior Publication Data

US 2005/0245438 A1 Nov. 3, 2005

Related U.S. Application Data

(63) Continuation of application No. PCT/US03/022600, filed on Jul. 18, 2003.

(60) Provisional application No. 60/398,521, filed on Jul. 24, 2002.

(51) Int. Cl.
*A61K 38/00* (2006.01)
(52) U.S. Cl. ...................... 530/311; 530/300
(58) Field of Classification Search ............... None
See application file for complete search history.

(56) References Cited

U.S. PATENT DOCUMENTS

| | | | |
|---|---|---|---|
| 4,372,884 A * | 2/1983 | Brown et al. ............... 530/311 |
| 5,073,541 A | 12/1991 | Taylor et al. ............... 514/9 |
| 5,436,155 A | 7/1995 | Bell et al. ............... 435/252.3 |
| 5,579,250 A | 11/1996 | Balaji et al. ............... 364/496 |
| 5,590,656 A | 1/1997 | O'Dorisio et al. |
| 5,597,894 A | 1/1997 | Coy et al. ............... 530/311 |
| 5,668,006 A | 9/1997 | Hadcock et al. ......... 435/252.3 |
| 5,708,135 A | 1/1998 | Coy et al. ............... 530/311 |
| 5,750,499 A | 5/1998 | Hoeger et al. ............... 514/9 |
| 5,929,209 A | 7/1999 | Hadcock et al. ............... 530/350 |
| 5,955,426 A | 9/1999 | Dean et al. ............... 514/11 |
| 5,972,308 A | 10/1999 | Dean ............... 424/1.69 |
| 5,976,496 A | 11/1999 | Dean et al. ............... 424/1.69 |
| 6,001,801 A | 12/1999 | Coy et al. ............... 514/9 |
| 6,017,509 A | 1/2000 | Dean et al. ............... 424/1.69 |
| 6,017,512 A | 1/2000 | Dean et al. ............... 424/1.69 |
| 6,051,206 A | 4/2000 | Dean et al. ............... 424/1.69 |
| 6,214,797 B1 | 4/2001 | Vale, Jr. et al. ............... 514/12 |
| 6,312,661 B1 | 11/2001 | Reubi ............... 424/1.69 |
| 6,564,152 B2 | 5/2003 | Ekins et al. ............... 702/19 |
| 6,579,967 B1 * | 6/2003 | Rivier et al. ............... 530/311 |
| 2001/0025097 A1 | 9/2001 | Sheridan et al. ............... 530/311 |
| 2002/0099506 A1 | 7/2002 | Floriano et al. ............... 702/19 |
| 2002/0133296 A1 | 9/2002 | Sem et al. ............... 702/19 |
| 2002/0137676 A1 | 9/2002 | Hsiang et al. |
| 2003/0073713 A1 | 4/2003 | Schoenhard ............... 514/282 |

FOREIGN PATENT DOCUMENTS

WO    WO 97/11962    *    4/1997

OTHER PUBLICATIONS

Rohrer, S., et al.; "Rapid Identification of Subtype-Selective Agonists of the Somatostatin Receptor Through Combinatorial Chemistry"; Science, vol. 282, pp. 737-740; Oct. 23, 1998; www.sciencemag.org.
Jiange, G, et al.; "Orthogonally Protected N-Methyl-Substituted a-Aminoglycines"; Protein and Peptide Letters. vol. 3, No. 4, pp. 219-224, 1996; Bentham Science Publishers B.V.; 0929-08665/94.
Smith-Jones, P., et al.; "DOTA-Lanreotide: A Novel Somatostatin Analog for Tumor Diagnosis and Therapy"; Endocrinology, vol. 140, No. 11, pp. 5136-5148, Copyright 1999 by The Endocrine Society; 0013-7227/99.

* cited by examiner

*Primary Examiner*—Cecilia J. Tsang
*Assistant Examiner*—Thomas S. Heard
(74) *Attorney, Agent, or Firm*—Fitch, Even, Tabin & Flannery

(57) ABSTRACT

Analogs of SRIF which are selective for SSTR4 in contrast to the other cloned SRIF receptors are useful in determining tissue and cellular expression of the receptor SSTR4 and its biological role in regulating tumor growth. SRIF analog peptides, such as des-AA$^{1,2,4,5,12,13}$[Ala$^7$]-SRIF; des-AA$^{1,2,4,5,12,13}$[Aph$^7$]-SRIF, des-AA$^{1,2,4,5,12,13}$[Aph$^7$] Cbm-SRIF; des-AA$^{1,2,4,5,12,13}$[Tyr$^2$,Ala$^7$]-Cbm-SRIF, and des-AA$^{1,2,4,5,12,13}$[Tyr$^7$,C$^\beta$Me-L-2Nal$^8$]-SRIF, and counterparts incorporating D-Cys$^3$ and/or D-Trp$^8$ and/or Ala$^{11}$, bind with high affinity to the cloned human receptor SSTR4 and activate the receptor, but they do not bind with significant affinity to human SSTR1, SSTR2, SSTR3 or SSTR5. By incorporating an iodinated tyrosine in position-2 in these SSTR4-selective SRIF analogs, a labeled compound useful in drug-screening methods is provided. Alternatively, for use in therapy, cytotoxins or highly radioactive elements can be N-terminally coupled or complexed thereto.

20 Claims, 2 Drawing Sheets

US 7,238,775 B2

RECEPTOR(SSTR4)-SELECTIVE SOMATOSTATIN ANALOGS

This application is a continuation of Ser. No. PCT/US2003/022600, filed Jul. 18, 2003, which claims priority from U.S. Provisional Ser. No. 60/398,521, filed Jul. 24, 2002 (the disclosures of which applications are incorporated by reference).

This invention was made with Government support under Grants Nos. DK-50124 and DK-59953 awarded by the National Institutes of Health. The Government has certain rights in this invention.

This invention is directed to peptides related to somatostatin and to methods for pharmaceutical treatment of mammals using such peptides. More specifically, the invention relates to shortened receptor-selective somatostatin analogs and the inclusion of an amino acid substitution in such analogs that confers receptor-selectivity thereto, to pharmaceutical compositions containing such peptides, to such peptides complexed with radioactive nuclides or conjugated to cytotoxins, to methods of diagnostic and therapeutic treatment of neoplastic and non-neoplastic mammalian diseases using such peptides, particularly peptides that are chelated or otherwise labeled, and to methods for screening for more effective drugs using such peptides.

BACKGROUND OF THE INVENTION

The cyclic tetradecapeptide somatostatin-14 (SRIF) was originally isolated from the hypothalamus and characterized as a physiological inhibitor of growth hormone release from the anterior pituitary. It was characterized by Guillemin et al. and is described in U.S. Pat. No. 3,904,594 as having the amino acid sequence: (cyclo 3-14)H-Ala-Gly-Cys-Lys-Asn-Phe-Phe-Trp-Lys-Thr-Phe-Thr-Ser-Cys-OH (SEQ ID NO:1). This tetradecapeptide has a bridging or cyclizing bond between the sulfhydryl groups of the two cysteinyl amino acid residues in the 3- and 14-positions. SRIF was found to also regulate insulin, glucagon and amylase secretion from the pancreas, and gastric acid release in the stomach, e.g. it inhibits the effects of pentagastrin and histamine on the gastric mucosa. SRIF is also expressed in intrahypothalamic regions of the brain and has a role in the regulation of locomotor activity and cognitive functions. SRIF is localized throughout the central nervous system, where it acts as a neurotransmitter. In the central nervous system, SRIF has been shown to both positively and negatively regulate neuronal firing, to affect the release of other neurotransmitters, and to modulate motor activity and cognitive processes.

Somatostatin and many analogs of somatostatin exhibit activity in respect to the inhibition of growth hormone (GH) secretion from cultured, dispersed rat anterior pituitary cells in vitro; they also inhibit GH, insulin and glucagon secretion in vivo in the rat and in other mammals. One such analog is [D-Trp$^8$]-SRIF, which is disclosed in U.S. Pat. No. 4,372,884. Somatostatin has also been found to inhibit the secretion of gastrin and secretin by acting directly upon the secretory elements of the stomach and pancreas, respectively, and somatostatin is being sold commercially in Europe for the treatment of ulcer patients. The powerful inhibitory effects of somatostatin on the secretion not only of GH but also of insulin and glucagon have led to studies of a possible role of somatostatin in the management or treatment of juvenile diabetes and have proved useful in studying the physiological and pathological effects of these hormones on human metabolism. SRIF is also known to inhibit the growth of certain tumors.

SRIF affects multiple cellular processes. Studies have shown that SRIF is an inhibitory regulator of adenylyl cyclase in different tissues. SRIF also regulates the conductance of ionic channels, including both $K^+$ and $Ca^{2+}$ channels. These actions of SRIF are mediated via pertussis toxin-sensitive guanine nucleotide-binding proteins. SRIF also regulates the activity of tyrosine phosphatases, the $Na^+/H^+$ antiport, and cellular proliferation through pertussis toxin-insensitive mechanisms.

SRIF induces its biological effects by interacting with a family of membrane-bound structurally similar receptors. Five SRIF receptors have been cloned and are referred to as SSTR1-5. Human SSTR1, mouse SSTR2 and mouse SSTR3 are described in Raynor et al., *Molecular Pharmacology*, 43, 838-844 (1993), and all five human SRIF receptors are now available for research purposes. Human SSTR1, 2 and 3 are also disclosed in U.S. Pat. No. 5,436,155. Additional SRIF receptors are disclosed in U.S. Pat. Nos. 5,668,006 and 5,929,209. All five receptors bind SRIF and SRIF-28 with high affinity. Selective agonists at SSTR2 and SSTR5 have been identified and used to reveal distinct functions of these receptors. These two receptors are believed to be the predominant subtypes in peripheral tissues. SSTR2 is believed to mediate the inhibition of growth hormone, glucagon and gastric acid secretion. In contrast, SSTR5 appears to be primarily involved in the control of insulin and amylase release. SSTR3 mediates inhibition of gastric smooth muscle contraction. SSTR4 is found in the pituitary, lungs, GI tract, kidneys, and in certain tumors to the substantial exclusion of the other SRIF receptors; it is believed to be activated upon binding by SRIF. These overall findings indicate that different receptor subtypes mediate distinct functions of SRIF in the body. Additional functions of SSTR4 could be learned if a highly selective agonist or antagonist was available.

There are different types of tissues in the human body that express somatostatin receptors including: (1) the gastrointestinal tract, likely including the mucosa and smooth muscle, (2) the peripheral nervous system, (3) the endocrine system, (4) the vascular system and (5) lymphoid tissue, where the receptors are preferentially located in germinal centers. In all these cases, somatostatin binding is of high affinity and specific for bioactive somatostatin analogs.

Somatostatin receptors are also expressed in pathological states, particularly in neuroendocrine tumors of the gastrointestinal tract. Most human tumors originating from the somatostatin target tissue have conserved their somatostatin receptors. It was first observed in growth hormone producing adenomas and TSH-producing adenomas; about one-half of endocrine inactive adenomas display somatostatin receptors. Ninety percent of the cardinoids and a majority of islet-cell carcinomas, including their metastasis, usually have a high density of somatostatin receptors. However, only 10 percent of colorectal carcinomas and none of the exocrine pancreatic carcinomas contain somatostatin receptors. The somatostatin receptors in tumors can be identified using in vitro binding methods or using in vivo imaging techniques; the latter allow the precise localization of the tumors and their metastasis in the patients. Because somatostatin receptors in gastroenteropancreatic tumors are functional, their identification can be used is to assess the therapeutic efficacy of an analog to inhibit excessive hormone release in the patients.

A cyclic SRIF analog, variously termed SMS-201-995 and Octreotide, i.e. D-Phe-c[Cys-Phe-D-Trp-Lys-Thr-Cys]-Thr-ol is being used clinically to inhibit certain tumor growth; analogs complexed with $^{111}$In or the like are also used as diagnostic agents to detect SRIF receptors expressed in cancers. Two similar octapeptide analogs having 6-membered rings, i.e. Lanreotide and Vapreotide, have also been developed, see Smith-Jones et al., *Endocrinology*, 140, 5136-5148 (1999). A number of versions of these somatostatin analogs have been developed for use in radioimaging or as radiopharmaceuticals in radionuclide therapy. For radioimaging, for example, labeling with $^{123}$I can be used as disclosed in U.K. Patent Application 8927255.3 and as described in Bakker et al., 1991, *J. Nucl. Med.*, 32:1184-1189. Proteins have been previously radiolabeled through the use of chelating agents, and there are various examples of complexing somatostatin analogs with $^{99}$Tc, $^{90}$Y or $^{111}$In, see U.S. Pat. Nos. 5,620,675 and 5,716,596. A variety of complexing agents have been used including DTPA; DOTA; HYNIC; and $P_2S_2$—COOH, U.S. Pat. No. 5,597,894 discloses analogs of Octreotide modified to facilitate radiolabeling.

Octreotide and other clinically used SRIF analogs interact significantly with three of the receptor subtypes, i.e. SSTR2, SSTR3 and SSTR5. SSTR2 and SSTR5 have recently been reported to mediate antiproliferative effects of SRIF on tumor cell growth; therefore, they may mediate the clinical effects of Octreotide in humans. U.S. Pat. No. 5,750,499 discloses SRIF analogs which are selective for SSTR1. A comprehensive review of SRIF and its receptors is found in Patel, Y. C. "Somatostatin and its receptor family", Front. *Neuroendocrinol*, 1999, 20, 157-198.

SSTR4 was one of the later SRIF receptors cloned; it is not found in the abundance in normal human tissue as are some of the other receptors. It has high affinity for SRIF and SRIF-28, while it exhibits low affinity for many synthetic analogs of SRIF. In certain human tumors, SSTR4 mRNA may be the most frequently and most strongly expressed subtype receptor among the SST receptors. As a result of the many tumors that carry SRIF receptors, peptide radiopharmaceuticals have been developed for detection and visualization of such tumors and in addition, compounds that complex with $^{111}$In or $^{90}$Y are proving to be very promising radioligands for receptor-mediated radiotherapy.

Because of the presence of SSTR4 on some tumors, and because of the otherwise ubiquitous nature of the somatostatin receptors, it would be valuable to have somatostatin analogs that would bind strongly to SSTR4 while at the same time showing only minimal propensity for binding to the other 4 receptors. The search has continued for somatostatin analogs which are more potent than somatostatin and/or exhibit dissociated inhibitory functions, and particularly for analogs which are selective for SSTR4. Non-peptide SRIF agonists have been identified using combinatorial chemistry which exhibit selectivity for each of SSTR1 to SSTR5, Rohrer, S. P. et al., *Science*, 282, 737-740, 23 Oct. 1998. However, no peptide ligand has thus far been available that selectively binds to SSTR4 and exhibits fairly high affinity; as a result, efforts to determine the precise localization of SSTR4 in the body and to identify more of its biological actions have been hindered. Moreover, such lack of selective SSTR4 peptide ligands having relatively high affinity has hampered efforts to design more selective tumor diagnosis and treatment and radionuclide therapy, because only peptide ligands can be satisfactorily derivatized to incorporate complexing agents for radionuclides.

SUMMARY OF THE INVENTION

Certain modifications have now been discovered which are effective to create peptide analogs of SRIF that are selective for SSTR4 in contrast to the other cloned SRIF receptors. The preferred modification substitutes Ala, Aph Amp or lamp into the 7-position of a shortened analog that otherwise binds to SSTR4; an alternative substitutes threo-L-C$^\beta$Me-2Nal into the 8-position of a SRIF analog and also preferably substitutes Tyr into the 7-position. The resultant peptides bind selectively to cloned SSTR4, and analogs of these peptides can be iodinated or otherwise radiolabeled while retaining their desirable biological properties. These novel peptides are useful in determining the tissue location and cellular expression of the receptor SSTR4 and its biological role in the endocrine, exocrine and nervous system, as well as in regulating certain pharmacological functions without the accompanying side effects heretofore characteristic of administering SRIF. These SRIF analog peptides, when radiolabeled, can be used in scintigraphy in order to locate, i.e. localize, tumors expressing these receptors, either in vitro or in vivo; other labels as well known in this art, e.g. fluorescent labels, can alternatively be used. With an appropriate chelated radioligand, these analogs can be turned into radiopharmaceuticals which are suitable for radionuclide therapy in treatment of such tumors; alternatively, they can be covalently joined to a cytotoxic moiety using an appropriate covalent conjugating agent, e.g. glutaraldehyde, or one which binds via a disulfide linkage or another non-severable linkage.

The SRIF analog peptides of the invention inhibit the binding of $^{125}$I-[Tyr$^{11}$]SRIF and $^{125}$I-[Leu$^8$,D-Trp$^{22}$,Tyr$^{25}$] SRIF-28 to the cloned human receptor SSTR4, but they do not strongly bind to SSTR1, SSTR2, SSTR3 or SSTR5. Additional of these SRIF analogs which incorporate an iodinated tyrosine in position 2 of the native molecule also do not bind to SSTR1, 2, 3 or 5 but still bind potently and saturably to SSTR4. This is also true for analogs to which $^{99}$Tc, $^{111}$In or $^{90}$Y, for example, has been chelated by linkers, such as DOTA or DTPA, or to which other complexing conjugating agents are linked to the N-terminus for the purpose of attaching moieties useful for diagnostic or therapeutic purposes. Tyr may alternatively be substituted into the 11-position and radioiodinated, but such is less preferred.

Preferred SRIF analogs not only bind selectively to SSTR4, but they bind thereto with high affinity. By selectively binding is meant that they exhibit a $K_D$ or an IC$_{50}$ with SSTR4 which is about one-tenth or less of that with respect to at least 3 of the five SRIF receptors and preferably with respect to all 4 other receptors. Most preferred analogs will be at least about 100 times more selective for SSTR4 than for any other SRIF receptor. It is believed the six residues located centrally within the ring structure, i.e. at positions 6-11 of the native molecule, are primarily responsible for receptor binding, biological activity and receptor selectivity.

These SRIF analogs can also be readily labeled and effectively used in drug screening methods and radionuclide or other cytotoxic therapy. For example, these analogs are useful in localizing such receptors in the body and in diagnosing the locations of tumors, particularly neuroendocrine tumors. As radionuclide therapeutic agents, they are considered to be particularly useful in combating tumors mediated by the SSTR4 receptors, as demonstrated by [$^{90}$Y-DOTA-Tyr$^3$]-Octreotide; however, they are able to accomplish this without the side effects, i.e. without destroying a substantial part of neighboring tissue, that would otherwise accompany administration of currently available Octreotide analogs which have a propensity to interact with a plurality of SRIF receptors such as SSTR2, SSTR3 and SSTR5.

In one particular aspect, the invention comprises a cyclic somatostatin (SRIF) analog peptide which selectively binds the SRIF receptor SSTR4, which peptide comprises the amino acid sequence (cyclo)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2) wherein $Xaa_1$ is des-Xaa, D-Ala, Ala, L-Hor, Cbm, an acyl group having up to 20 carbon atoms or alkyl($C_1$ to $C_6$); $Xaa_2$ is Tyr, D-Tyr, Gly or des-Xaa; $Xaa_3$ is Cys or D-Cys; $Xaa_4$ is Lys or des-Xaa; $Xaa_5$ is Asn or des-Xaa; $Xaa_7$ is an amino acid selected from the group consisting of Ala, Aph, Amp, lamp, Val or Tyr; $Xaa_8$ is an amino acid selected from the group consisting of (A)Trp, (A)D-Trp, 2Nal and threo-L-$C^\beta$Me-2Nal, wherein A is H, Cl, F, Br, Me, $NO_3$, OMe or formyl; $Xaa_{11}$ is Ala, Gly, Val, Phe or Tyr; $Xaa_{12}$ is Thr or des-Xaa; and $Xaa_{13}$ is Ser, D-Ser or des-Xaa; provided that when $Xaa_7$ is Tyr, $Xaa_8$ is threo-L $C^\beta$Me-2Nal. A cytotoxic or radioactive moiety may be linked at the N-terminus as known in this art.

In another particular aspect, the invention comprises a cyclic somatostatin (SRIF) analog peptide having specific affinity for the SRIF receptor SSTR4, which peptide has an amino acid sequence at least 8 residues in length, contains a Cys-Cys disulfide bond with a sequence of at least 6 residues located between said Cys residues as a ring which includes Phe-$Xaa_7$-$Xaa_8$-Lys-Thr-$Xaa_{11}$ (SEQ ID NO:10) or its equivalent adjacent the Cys residue near the N-terminus, which analog peptide is characterized by the presence of $Xaa_7$ in the form of Ala, Aph, Amp or lamp, $Xaa_8$ being (A)Trp, (A)D-Trp or 2Nal, wherein A is H, Cl or F and B is H, Cl, F or $NO_3$, and $Xaa_{11}$ being Ala, Phe or Tyr.

The present invention further provides a new method of screening for ligands that are selective for SSTR4 using a pharmacophore model that is premised upon a pattern of ligand features that are determined to be required for selective binding.

In a further particular aspect, the invention comprises a method of detecting, in the body of a human being, tumors having SSTR4 and their metastases in tissues, which in healthy condition and in non-neoplastic conditions of chronic inflammation do not contain substantial quantities of SSTR4, which method comprises (i) administering to said human, in a quantity sufficient for external imaging, a composition comprising a peptide according to claim 1, said peptide being labeled with (a) a radioactive metal isotope or (b) a paramagnetic metal atom or (c) a radioactive halogen isotope, and thereupon (ii) subjecting said human to external imaging, by radioactive scanning or by magnetic resonance imaging, to determine the targeted sites in the body thereof in relation to the background activity, in order to allow detection and localization of said tumors in the body.

DETAILED DESCRIPTION OF THE PREFERRED EMBODIMENTS

Figure 1:
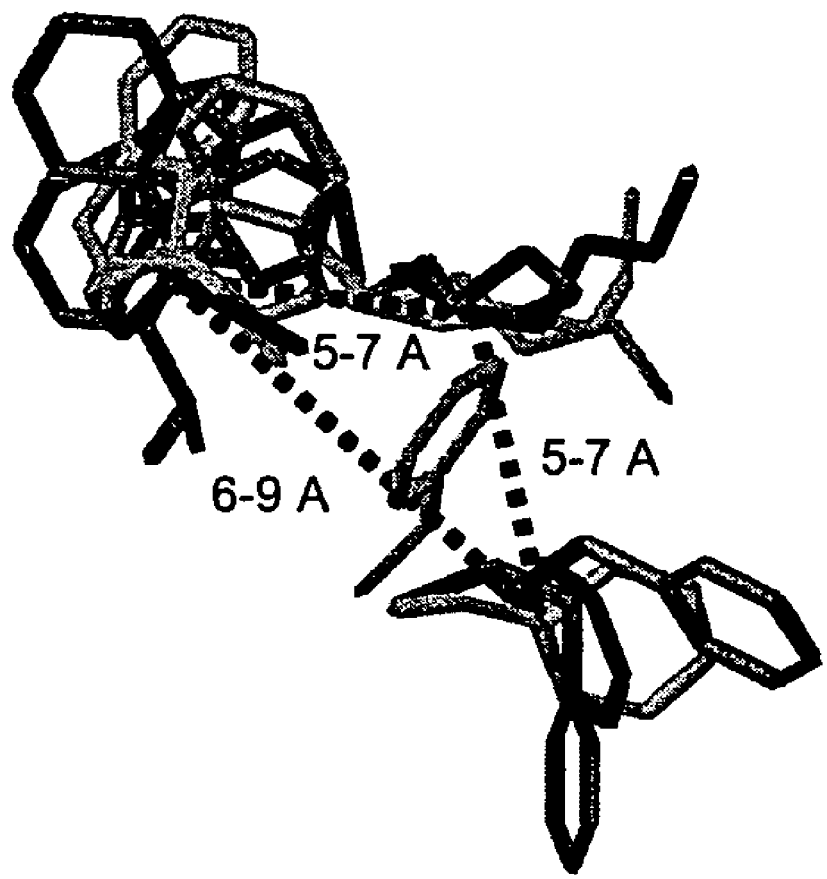
FIG. 1 is a view of a structural motif showing the superimposition of side chains of several SSTR4-selective analogs of SRIF.

The standard 3-letter abbreviations identify the alpha-amino acid residues, and where the amino acid residue has isomeric forms, it is the L-form of the amino acid that is represented unless otherwise expressly indicated, e.g. Ser=L-serine. By D,L or D/L or L/D is meant a mixture of the D- and L-isomers of a particular α-amino acid. By "threo-" is meant an amino acid having two chiral centers with opposite optical configurations. By "erythro-" is meant an amino acid having two chiral centers with the same optical configurations. When reference is hereinafter made to a position in the peptide, such is meant to refer to the corresponding position of the native peptide.

SRIF analog peptides are provided having a selective affinity for the SRIF receptor SSTR4; the preferred analogs also have a high affinity for SSTR4, i.e. equal to a $K_D$ of about 10 nanomolar or less. These peptides broadly encompass known analogs of SRIF, or obvious variations thereof, which either have a residue of Ala, Aph (aminophenylalanine), Amp (aminomethylphenylalanine) Iamp (isopropylamino-methylphenylalanine) in the 7-position or have threo-L-$C^\beta$Me-2Nal in the 8-position peptide and preferably have Tyr the 7-position. In the first instance, the 8-position residue may be Trp, D-Trp, substituted Trp or D-Trp, or 2Nal. So long as a peptide analog which is being modified exhibits SRIF properties by binding to SRIF receptors, insertion of such residues in the corresponding 7- and/or 8-positions will create a molecule which is highly selective for the SSTR4 receptor. Preferably the 1-, 2-, 4-, 5-, 12- and 13-position residues are deleted from the 14-residue native SRIF to increase binding affinity to SSTR4, i.e. creating octapeptides.

Since the characterization of SRIF, a large number of SRIF analogs have been synthesized having increased potency in some respect. The following U.S. patents are illustrative of such SRIF analogs, which analogs can be rendered selective for the SSTR4 receptor by the incorporation of the modification of the present invention: U.S. Pat. Nos. Re. 30,548; 4,133,782; 4,211,693; 4,316,891; 4,372,884; 4,393,050; 4,061,608; 4,081,433; 4,182,707; 4,190,575; 5,185,010; 4,215,039; 4,230,617; 4,238,481; 4,253,998; 4,282,143; 4,328,214; 4,358,439; 4,209,441; 4,210,636; 4,316,890; and 5,073,541.

Examples of representative peptides exhibiting the desired specificity for SSTR4 are provided by the following amino acid sequence, which is based upon a numbering system consistent with the 14-residue sequence of native mammalian SRIF, wherein the residues at positions 4-5 and 12-13 are preferably eliminated: (cyclo 3-14)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2) wherein $Xaa_1$ is des-Xaa, Ala, D-Ala, L-Hor, Cbm, an acyl group having up to 20 carbon atoms, e.g. 4-hydroxybenzoyl, or alkyl ($C_1$ to $C_6$); $Xaa_2$ is Tyr, D-Tyr, Gly or des-Xaa; $Xaa_3$ is Cys or D-Cys; $Xaa_4$ and $Xaa_5$ are des-Xaa; $Xaa_7$ is an amino acid selected from the group consisting of Ala, Aph, Amp, lamp, Val or Tyr; $Xaa_8$ is an amino acid selected from the group consisting of Trp (substituted or unsubstituted), D-Trp (substituted or unsubstituted), 2Nal and threo-L-$C^\beta$Me-2Nal; $Xaa_{11}$ is Phe, Ala, Gly, Val or Tyr; and $Xaa_{12}$ and $Xaa_{13}$ are des-Xaa; provided that when $Xaa_7$ is Tyr, $Xaa_8$ is threo-L-$C^\beta$Me-2Nal. A tyrosine residue at position 2, 7 or 11 may be radioiodinated, with iodination of $Tyr^2$ being preferred. As previously indicated, a complexing agent can be linked to the α-amino group at the N-terminus of any of these peptide analogs which is capable of joining a radioactive nuclide or a cytotoxin thereto. For example, a chelator such as DOTA can be added at the N-terminus either by joining it directly to Cys³ or indirectly thereto using a linker such as GABA (gamma amino butyric acid) (see e.g. U.S. Pat. No. 6,022,523).

One preferred subgenus of SRIF analogs comprises the amino acid sequence: (cyclo 3-14)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2) wherein $Xaa_1$ is des-Xaa; $Xaa_2$ is Tyr, D-Tyr or des-Xaa; $Xaa_7$ is Ala or Aph; and $Xaa_8$ is Trp, D-Trp or 2Nal; and $Xaa_{11}$ is Ala or Phe. The remaining Xaa groups are as defined hereinbefore whenever not specified.

Another preferred subgenus of SRIF analogs comprises the amino acid sequence: (cyclo 3-14)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2) wherein $Xaa_1$ is Cbm or des-Xaa; $Xaa_2$ is Tyr, D-Tyr or des-Xaa; $Xaa_7$ is Ala or Aph; $Xaa_8$ is Trp or D-Trp; and $Xaa_{11}$ is Ala or Phe.

A further preferred subgenus of SRIF analogs comprises the amino acid sequence: (cyclo)$Xaa_1$-Tyr-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2), where $Xaa_1$ is Ac, Cbm or des-Xaa; $Xaa_3$ is Cys or D-Cys; $Xaa_7$ is Ala, Aph or Amp; $Xaa_8$ is Trp, D-Trp or 2Nal, $Xaa_{11}$ is Ala, Phe or Tyr, and $Xaa_4$, $Xaa_5$, $Xaa_{12}$ and $Xaa_{13}$ are des-Xaa.

An additional preferred subgenus of SRIF analogs comprises the amino acid sequence: (cyclo 3-14)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2) wherein $Xaa_1$ is des-Xaa; $Xaa_2$ is Tyr, D-Tyr or des-Xaa; $Xaa_7$ is Tyr; $Xaa_8$ is threo-L-$C^\beta$Me-2Nal.

By D/L-2Nal is meant a mixture of L-isomers and D-isomers of alanine which is substituted by naphthyl on the β-carbon atom. 2Nal, wherein the attachment to naphthalene is at the 2-position on the ring structure, is preferred; however, 1Nal is generally equivalent. Likewise for purposes of this application, reference to Trp and D-Trp in the description other than in a specific example should be understood to include the unsubstituted residue as well as a residue where a single substitution for hydrogen is made in either the 5- or 6-position on Trp, with such substituents being selected from chloro, fluoro, bromo, methyl, nitro and methoxy, with chloro, fluoro and nitro being preferred, or alternatively where the indole nitrogen is acylated with formyl (1For-). By Me is meant methyl, and by Cbm is meant carbamoyl. By Bzl is meant benzyl, and by Bz is meant benzoyl. By Hor is meant the L-isomer of hydroorotic acid. By Aph is meant aminophenylalanine, where the amino group is preferably attached to the 4-position on the phenyl ring, but attachment at either the 2- or 3-position is equivalent. By Amp is meant Phe with an aminomethyl substitution at the 4- or 3-position on the phenyl ring; by Iamp is meant the isopropyl-substituted version thereof. By SRIF is meant the 14-residue cyclic peptide somatostatin.

The C-terminus is usually free acid, although an equivalent, e.g. OMe or $NH_2$, might be used. The N-terminus may be modified in various ways without significantly adversely effecting the binding affinity, all of which modifications in these cyclic peptides are considered to be included as a part of the peptides of the overall invention. For example, a variety of additions may be made to the N-terminal amino acid in the form of complexing or conjugating agents which can be then used to join a desired moiety to the peptide. For example, chelating agents, such as DTPA, DOTA, HYNIC and $P_2S_2$—COOH may be attached; alternatively, a cytotoxin may be covalently linked thereto via a conjugating agent if desired. When either Tyr or D-Tyr appears at the N-terminus, it may be in the "desamino" form and/or may be radioiodinated or otherwise labeled. Acyl groups having not more than about 20 amino acids, e.g. 4-hydroxybenzyl, may also be present at the N-terminus, as bulky moieties appear to be accommodated without loss of selectivity.

Identification of the biological and pharmacological properties of SSTR4 has lagged somewhat behind the other SRIF receptors because of the lack of ligands which are significantly selective for SSTR4. The peptides of the invention are believed to be the first truly SSTR4-selective peptides, and for a number of reasons (as earlier mentioned), it is considered advantageous to have peptide, rather than non-peptide, ligands of this character. They will be very helpful in determining the many functional roles of this receptor and in selectively binding only this SRIF receptor and not the others, and they will be particularly valuable in SRIF receptor-targeted scintigraphy and radionuclide therapy.

Selectivity for binding of the analog peptides of the invention to SSTR4 has been demonstrated by testing their interaction with the five different cloned human SRIF receptors as described in great detail hereinafter. Generally, recombinant cells expressing the receptor are washed and homogenized to prepare a crude protein homogenate in a suitable buffer, as known in the art. In a typical assay, an amount of protein from the cell homogenate is placed into a small volume of an appropriate assay buffer at an appropriate pH. Candidate substances, such as potential SRIF agonists and antagonists, are added to the admixture in convenient concentrations, and the interaction between the candidate substance and the receptor polypeptide is monitored. The peptides of the invention bind substantially strongly only to SSTR4, and their binding exhibits high affinity.

Receptor binding assays are performed on cloned SRIF receptors, and competitive assays are used to generate $IC_{50}$ values which are indicative of the concentration of a competitive ligand necessary to displace a saturation concentration of a target ligand being measured from 50% of binding sites. The peptide des-$AA^{1,2,4,5,12,13}$-[$Ala^7$]SRIF inhibits the binding to SSTR4 of an iodinated SRIF-28 ligand that has strong affinity for all five receptors. Testing shows that it binds to the cloned human SSTR4 with an $IC_{50}$ of about 0.84±0.2, while this SRIF analog peptide does not bind to human SSTR1, SSTR2, or SSTR3 at concentrations below about 750 nM nor to SSTR5 at a concentration below 630 nM.

When this SRIF analog is modified to have a tyrosine residue in position-2 which is then iodinated, testing for binding to the cloned human SRIF receptors shows the I-$Tyr^2$ analog likewise did not significantly bind to SSTR1, 2, 3 or 5, but continues to bind saturably to SSTR4. These SRIF analogs that selectively bind to SSTR4 with high affinity are considered to be particularly useful in combating tumors by carrying radionuclides, e.g. $^{125}I$, to the sites of these receptors without destroying a substantial part of neighboring healthy tissue having other SRIF receptors.

As hereinbefore indicated, SSTR4 mRNA has been detected in a variety of tumors. However, it is presently not known whether SSTR4 plays a major role in tumor growth regulation and, if it does, whether it mediates simulation or inhibition. Therefore, it is difficult to foretell whether a selective SSTR4 antagonist would have a beneficial role for long-term treatment of tumors. However, the use of SRIF analogs selective for SSTR4 that bind strongly thereto, and that are long-acting can be effectively used to destroy such tumors or other pathogenic cells via radionuclide or cytotoxic therapy. To date the use of Octreotide in the treatment of such tumors has not been considered to be satisfactorily effective.

Although an analog of Octreotide has been employed to detect human tumors having high expression of SRIF receptors through the use of positron-emission tomography, this SRIF analog does not distinguish among SSTR2, SSTR3 and SSTR5. In comparison, radiolabeled SRIF analogs of the present invention can be employed for such a purpose, and they are considered to be specifically useful in identifying tumors expressing SSTR4, which tumors are then therapeutic targets for treatment with SSTR4-selective ligands as mentioned hereinbefore.

Thus, according to one aspect of the present invention, a method of intraoperatively detecting malignant tumors in the body of a human being in tissues which in healthy condition do not contain substantial quantities of SSTR4 comprises (i) administering to such being a composition comprising, in a quantity sufficient for detection by a gamma detecting probe, an SSTR4-selective peptide, said peptide being radioactively labeled, e.g. with $^{161}$Tb, $^{90}$Y, $^{177}$Lu, $^{123}$I or $^{125}$I and (ii) after allowing the active substance to be bound and taken up in said tumors and after blood clearance of radioactivity, subjecting such being to a radioimmunodetection technique in the relevant area of the body by using a gamma-detecting probe.

The SRIF analogs of the present invention are the first peptide analogs truly selective for SSTR4 and are considered to be useful in combating cancers which express SSTR4. They are also considered to be most useful in scintigraphy to determine the distribution of cells and tissues expressing this receptor in the brain and in the endocrine and exocrine systems, and also in identifying selective functions of this receptor in the body. They are further useful in selectively carrying out certain of the pharmacological effects mediated by SSTR4 for which SRIF has been found useful over the past 2 decades.

These analogs can also be used for the therapeutic treatment of malignant tumors in the body of a human being in tissues which in healthy condition do not contain substantial quantities of SSTR4; such being is administered a composition which includes, in a quantity effective for combating or controlling tumors, an SSTR4-selective peptide labeled with an isotope selected from the group consisting of $^{186}$Re, $^{188}$Re, $^{71}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{114}$Ag, $^{124}$I and $^{131}$I.

Figure 2:
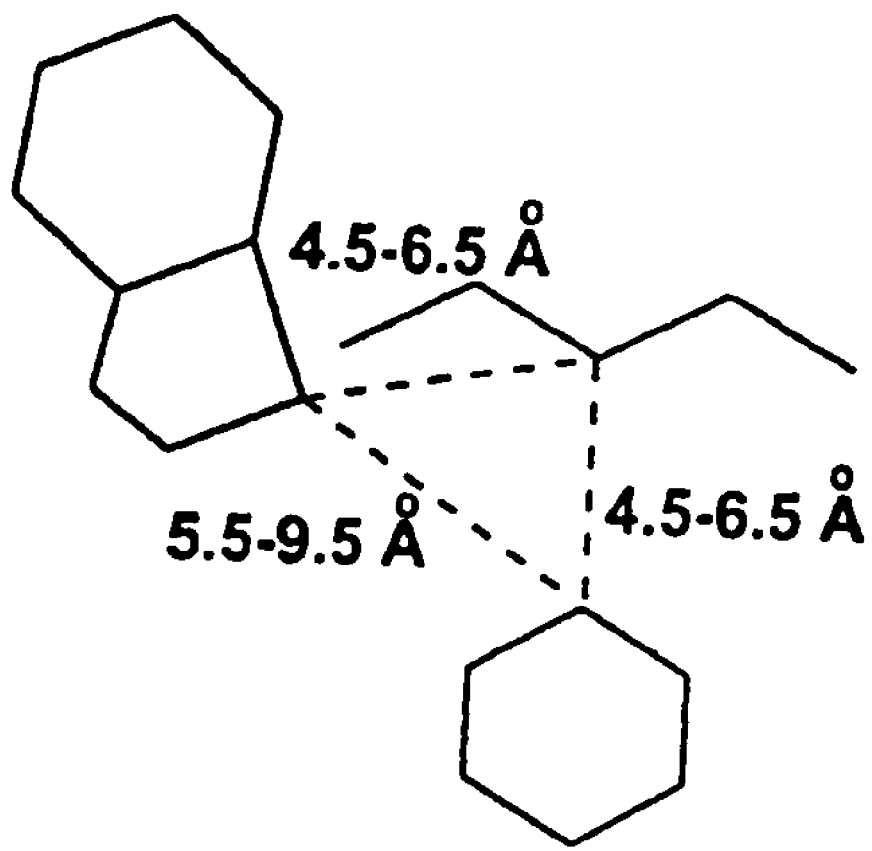
FIG. 2 is a schematic drawing of the pharmacophore model for SSTR4-selective analogs of SRIF.

Labeled SRIF analogs of the invention are also considered to be useful in drug-screening assays to screen for new effective peptide and non-peptide agents which will bind with high affinity to SSTR4 and which may be either highly effective agonists or antagonists. Once a known ligand for the receptor SSTR4 is in hand, one can obtain a baseline activity for the recombinantly produced receptor. Then, to test for inhibitors or modifiers, i.e. antagonists of the receptor function, one can incorporate into a test mixture a candidate substance to test its effect on the receptor. Such candidate ligands can be identified using the pharmacophore model described hereinafter which is shown in FIG. 2. By comparing reactions which are carried out in the presence or absence of the candidate substance, one can then obtain information regarding the effect of the candidate substance on the normal function of the receptor. The cyclic SRIF analogs described in Examples 2-7 hereinafter are agonists and can be employed to activate SSTR4 to carry out its normal function.

The peptides of the present invention can be synthesized by classical solution synthesis, but they are preferably synthesized by solid-phase technique. A chloromethylated resin or a hydroxymethylated resin is preferably used. For example, these peptides having a free carboxyl C-terminus are preferably synthesized as taught in U.S. Pat. No. 4,816,438. Solid-phase synthesis is conducted in a manner to stepwise add amino acids in the chain beginning at the C-terminus in the manner set forth in that U.S. patent. Side-chain protecting groups, which are well known in the art, are preferably included as a part of any amino acid which has a particularly reactive side chain, and optionally may be used in the case of others such as Trp, when such amino acids are coupled onto the chain being built upon the resin. Such synthesis provides a fully protected intermediate peptidoresin. Generally, protecting groups are split off and the peptide is cleaved from the resin support before oxidizing to create a disulfide bond between the Cys side chains.

The SRIF analogs of the invention are generally effective at levels of less than 100 micrograms per kilogram of body weight. For prolonged action, it may be desirable to use dosage levels of about 0.1 to about 2.5 milligrams per kilogram of body weight. These analogs are soluble in water and thus can be prepared as relatively concentrated solutions for administration.

The following Examples illustrate the syntheses of a number of SRIF analog peptides embodying various features of the invention. In each peptide, the cysteine residues in positions 3 and 14 are joined by the cyclizing disulfide bond.

EXAMPLE 1

The somatostatin analog des-AA$^{1,2,4,5,12,13}$[4Aph$^{7}$]-SRIF having the structure: (cyclo)H-Cys-Phe-4Aph-Trp-Lys-Thr-Phe-Cys-OH (SEQ ID NO:3) is synthesized by the solid phase methodology in a stepwise manner on a chloromethylated resin generally as described in Example 2 of the '499 patent. For the 7-position residue, N$^\alpha$Boc-4-Aph(Fmoc) is coupled into the chain. This synthesis creates the intermediate: Boc-Cys(Mob)-Phe-4Aph(Fmoc)-Trp-Lys(Cl-Z)-Thr(Bzl)-Phe-Cys(Mob)-O—CH$_2$-resin support.

After removal of the Fmoc group with 20% piperidine in NMP, cleavage of the peptide from the resin and deprotection of the remaining side chain protecting groups are performed in hydrofluoric acid (HF) (25 ml) in the presence of 10% anisole and 5% methylsulfide for 1 hour at 0° C. After elimination of hydrofluoric acid under high vacuum, the resin-peptide is washed with anhydrous diethyl ether.

The resin is immediately extracted with 75% acetic acid (200 ml). The extract is filtered into a 500 milliliter round-bottom flask and is then oxidized to create the disulfide cyclic linkage by stirring vigorously while rapidly adding a 10 weight percent solution of iodine in methanol until the resultant solution remains orange-colored. It is then stirred for 40 additional minutes and quenched with 10% ascorbic acid in water until the yellow color is gone. Concentration under vacuum is carried out to reduce the volume to about 50 milliliters, followed by dilution to about 300 milliliters with 60% acetonitrile/40% water/0.1% TFA. The resultant solution is frozen and lyophilized.

The lyophilized crude peptides were purified by preparative RP-HPLC using a linear gradient 1% B per 3 min increase from the baseline % B (Eluent A=0.25 N TEAP pH 2.25, eluent B=60% CH$_3$CN, 40% A) at a flow rate of 100 mL/min. Peaks are located, which are then individually purified using buffer systems as disclosed in Hoeger et al., *Biochromatography*, 2, 134-142 (1987). Purification in TEAP pH 2.25 was followed by a rechromatography in a 0.1% TFA solution and acetonitrile on the same cartridge (gradient of 1% acetonitrile/min). The separations were monitored by analytical RP-HPLC at 215 nm. The fractions containing the pure product were pooled and lyophilized to obtain a fluffy white powder. The desired cyclic octapeptide (cyclo)H-Cys-Phe-4Aph-Trp-Lys-Thr-Phe-Cys-OH is obtained which appears to be greater than 97% pure on capillary zone electrophoresis.

MS analysis shows an [M+H]$^+$ mass of 1094.3 Da which compares favorably to the calculated mass of 1093.45 Da. The peptide is hereinafter referred to as Peptide No. 1.

EXAMPLE 2

The initial synthesis described in Example 1 is repeated with one change; N$^\alpha$Boc-D-Trp is used to provide the 8-position residue.

Cleavage, deprotection, cyclization and purification are then carried out as in Example 1. The purified cyclic octapeptide has the formula: (cyclo)H-Cys-Phe-4Aph-D-Trp-Lys-Thr-Phe-Cys-OH, has a purity on CZE of about 98%, and is referred to as Peptide No. 2. MS analysis shows an [M+H]$^+$ mass of 1094.3 Da, which compares favorably with the calculated value of 1093.45 Da.

EXAMPLE 3

The synthesis described in Example 1 is repeated with one change. Following removal of the Boc group at the N-terminus, a reaction is carried out to add a carbamoyl (Cbm) moiety and thus create an urea group at the N-terminus.

After deblocking the α-amino group at the N-terminus using trifluoroacetic acid (TFA), a reaction is carried out with about 1 gm of the peptidoresin and 100 mg of sodium cyanate (NaOCN) and acetic acid (3 ml) for 30 minutes at 22° C. in NMP (4 ml). This reaction results in the addition of the carbamoyl moiety at the N-terminus. Thereafter, cleavage of the peptide from the resin and deprotection of the side chain protecting groups, followed by cyclization and purification, are carried out as in Example 1. The purified cyclic octapeptide has the formula: (cyclo)Cbm-Cys-Phe-4Aph-Trp-Lys-Thr-Phe-Cys-OH (SEQ ID NO:3), has a purity on CZE of about 92% and is referred to as Peptide No. 3. MS analysis shows an [M+H]$^+$ mass of 1137.4 Da, which compares favorably to the calculated value of 1136.46 Da.

EXAMPLE 4

The synthesis set forth in Example 3 is repeated substituting Boc-D-Trp for the 8-position residue. Cleavage, deprotection, cyclization and purification of the peptide are carried out as in Example 1. The purified cyclic peptide has the formula: (cyclo)Cbm-Cys-Phe-4Aph-D-Trp-Lys-Thr-Phe-Cys-OH, has a purity on CZE of about 98%, and is referred to as Peptide No. 4. MS analysis shows an [M+H]$^+$ mass of 1137.2 Da, which compares favorably to the calculated value of 1136.46 Da.

EXAMPLE 5

The synthesis described in Example 1 is repeated with one change; instead of using N$^\alpha$Boc-Trp for the 8-position residue, N$^\alpha$Boc-2Nal is used. Cleavage, deprotection, cyclization and purification are carried out as in Example 1. A purified cyclic peptide having the formula: (cyclo)H-Cys-Phe-4Aph-2Nal-Lys-Thr-Phe-Cys-OH (SEQ ID NO:4) is obtained which appears to be greater than 99% pure on capillary zone electrophoresis. It is referred to as Peptide 5.

MS analysis shows an [M+H]$^+$ mass of 1105.4 Da which compares favorably with the calculated value of 1104.46 Da.

EXAMPLE 6

The synthesis described in Example 1 is repeated with one change. Following removal of the Boc group at the N-terminal, the peptide is elongated by one residue by reaction with N$^\alpha$Boc-Tyr(2BrZ) to provide a tyrosine residue at the N-terminus. Thereafter, cleavage of the peptide from the resin and deprotection of the side chain protecting groups, followed by cyclization and purification, are carried out as in Example 1. The purified cyclic nonapeptide has the formula: (cyclo)H-Tyr-Cys-Phe-4Aph-Trp-Lys-Thr-Phe-Cys-OH (SEQ ID NO:5), has a purity on CZE of about 98% and is referred to as Peptide No. 6. MS analysis shows an [M+H]$^+$ mass of 1257.5 Da, which compares favorably to the calculated value of 1256.51 Da.

EXAMPLE 7

The synthesis set forth in Example 6 is repeated substituting N$^\alpha$Boc-D-Trp for the 8-position residue. Cleavage, deprotection, cyclization and purification of the peptide are carried out as in Example 1. The purified cyclic peptide has the formula: (cyclo)H-Tyr-Cys-Phe-4Aph-D-Trp-Lys-Thr-Phe-Cys-OH, has a purity on CZE of about 98% and is referred to as Peptide No. 7. MS analysis shows an [M+H]$^+$ mass of 1257.6 Da, which compares favorably to the calculated value of 1256.51 Da.

EXAMPLE 8

The synthesis described in Example 6 is repeated with one change. Following removal of the Boc group at the N-terminus, a reaction is carried out to add a carbamoyl moiety and thus create an urea group at the N-terminus using the process described in Example 3.

This reaction results in the addition of the carbamoyl moiety to the tyrosine residue at the N-terminus. Thereafter, cleavage of the peptide from the resin and deprotection of the side chain protecting groups, followed by cyclization and purification, are carried out as in Example 1. The purified cyclic nonapeptide has the formula: (cyclo)Cbm-Tyr-Cys-Phe-4Aph-Trp-Lys-Thr-Phe-Cys-OH (SEQ ID NO:5), has a purity on CZE of about 92%, and is referred to as Peptide No. 8. MS analysis shows an [M+H]$^+$ mass of 1300.6 Da, which compares favorably to the calculated value of 1299.52 Da.

EXAMPLE 9

The synthesis described in Example 1 is repeated with one change; instead of using N$^\alpha$Boc-Phe for the 11-position residue, N$^\alpha$Boc-Tyr(2BrZ) is used. Cleavage, deprotection, cyclization and purification are carried out as in Example 1. A purified cyclic peptide having the formula: (cyclo)H-Cys-Phe-4Aph-Trp-Lys-Thr-Tyr-Cys-OH (SEQ ID NO:6) is obtained which appears to be greater than 97% pure on capillary zone electrophoresis. It is referred to as Peptide 9. MS analysis shows an [M+H]$^+$ mass of 1110.4 Da which compares favorably with the calculated value of 1109.45 Da.

EXAMPLE 10

The synthesis set forth in Example 3 is repeated substituting Boc-Tyr(2BrZ) for the 11-position residue. Cleavage, deprotection, cyclization and purification of the peptide are carried out as in Example 1. The purified cyclic peptide has the formula: (cyclo)Cbm-Cys-Phe-4Aph-Trp-Lys-Thr-Tyr-Cys-OH (SEQ ID NO:6), has a purity on CZE of about 90%, and is referred to as Peptide No. 10. MS analysis shows an [M+H]$^+$ mass of 1153.4 Da, which compares favorably to the calculated value of 1152.45 Da.

EXAMPLE 10A

The synthesis described in Example 10 is repeated with one change. Instead of using N$^\alpha$Boc-Trp for the 8-position residue, N$^\alpha$Boc-D-Trp is used. Cleavage, deprotection, cyclization and purification of the peptide are carried out as in Example 1. The purified cyclic peptide has the formula (cyclo)Cbm-Cys-Phe-4Aph-D-Trp-Lys-Thr-Tyr-Cys-OH, has a purity on CZE of about 98%, and is referred to as Peptide No. 10A. MS analysis shows an [M+H]$^+$ mass of 1153.4 Da which compares favorably to the calculated value of 1152.45 Da.

EXAMPLE 11

The synthesis described in Example 1 is repeated with two changes; instead of using N$^\alpha$Boc-4Aph(Fmoc) for the 7-position residue, N$^\alpha$Boc-Ala is used, and N$^\alpha$Boc-D-Trp is used for the 8-position residue. Cleavage, deprotection, cyclization and purification are carried out as in Example 1. A purified cyclic peptide having the formula: (cyclo)H-Cys-Phe-Ala-D-Trp-Lys-Thr-Phe-Cys-OH is obtained which appears is to be greater than 93% pure on capillary zone electrophoresis. It is referred to as Peptide 11. MS analysis shows an [M+H]$^+$ mass of 1003.5 Da which compares favorably with the calculated value of 1002.41 Da.

EXAMPLE 11A

The synthesis described in Example 1 is repeated with one change; instead of using N$^\alpha$Boc-4-aminoPhe(Fmoc) for the 7-position residue, N$^\alpha$Boc-Val is used. Cleavage, deprotection, cyclization and purification are carried out as in Example 1. A purified cyclic peptide having the formula: (cyclo)H-Cys-Phe-Val-D-Trp-Lys-Thr-Phe-Cys-OH is obtained. It is referred to as Peptide 11A and is selective in binding to hSSTR$_4$ as compared with its binding affinity to the other 4 receptors.

EXAMPLE 12

The synthesis described in Example 11 is repeated with one change; N$^\alpha$Boc-L-Trp is used to provide the 8-position residue.

Cleavage, deprotection, cyclization and purification are then carried out as in Example 1. The purified cyclic octapeptide has the formula: (cyclo)H-Cys-Phe-Ala-Trp-Lys-Thr-Phe-Cys-OH (SEQ ID NO:7) has a purity on CZE of about 98%, and is referred to as Peptide No. 12. MS analysis shows an [M+H]$^+$ mass of 1003.4 Da which compares favorably with the calculated value of 1002.41 Da.

EXAMPLE 12A

The synthesis described in Example 12 is repeated with one change; instead of using N$^\alpha$Boc-Phe for the 11-position residue, N$^\alpha$Boc-Ala is used. Cleavage, deprotection, cyclization and purification are carried out as in Example 1. A purified cyclic peptide having the formula: (cyclo)H-Cys-Phe-Ala-Trp-Lys-Thr-Ala-Cys-OH (SEQ ID NO: 11) is obtained which appears to be greater than 98% pure on capillary zone electrophoresis. It is referred to as Peptide 12A. MS analysis shows an [M+H]$^+$ mass of 927.3 Da which compares favorably with the calculated value of 926.38 Da.

EXAMPLE 12B

The synthesis described in Example 12A is repeated with one change. Instead of using N$^\alpha$Boc-Trp for the 8-position residue, N$^\alpha$Boc-D-Trp is used. Cleavage, deprotection, cyclization and purification of the peptide are carried out as in Example 1. The purified cyclic peptide has the formula (cyclo)Cys-Phe-Ala-D-Trp-Lys-Thr-Ala-Cys-OH, has a purity on CZE of about 99%, and is referred to as Peptide No. 12B. MS analysis shows an [M+H]$^+$ mass of 927.3 Da which compares favorably to the calculated value of 926.38 Da.

EXAMPLE 12C

The synthesis described in Example 12 is repeated with one change; at the end of the synthesis, DOTA is added as a chelator. Cleavage, deprotection, cyclization and purification are carried out as in Example 1. A purified cyclic peptide having the formula: (cyclo)DOTA-Cys-Phe-Ala-Trp-Lys-Thr-Phe-Cys-OH (SEQ ID NO: 7) is obtained. It is referred to as Peptide 12C. It continues to show selectivity in binding to hSSTR$_4$ as compared with its binding affinity to the other 4 receptors.

EXAMPLE 12D

The synthesis described in Example 12C is repeated with one change; instead of coupling DOTA directly to Cys, it is coupled through GABA as a linker. Cleavage, deprotection, cyclization and purification are carried out as in Example 1. A purified cyclic peptide having the formula: (cyclo)DOTA-GABA-Cys-Phe-Ala-Trp-Lys-Thr-Phe-Cys-OH (SEQ ID NO: 7) is obtained. It is referred to as Peptide 12D. It continues to show selectivity in binding to hSSTR$_4$ as compared with its binding affinity to the other 4 receptors.

EXAMPLE 12E

The synthesis described in Example 12 is repeated with one change; instead of using N$^\alpha$Boc-Phe for the 11-position residue, N$^\alpha$Boc-Val is used. Cleavage, deprotection, cyclization and purification are carried out as in Example 1. A purified cyclic peptide having the formula: (cyclo)H-Cys-Phe-Ala-Trp-Lys-Thr-Val-Cys-OH (SEQ ID NO: 12) is obtained. It is referred to as Peptide 12E and is selective in binding to hSSTR$_4$ as compared with its binding affinity to the other 4 receptors.

EXAMPLE 12F

The synthesis described in Example 12E is repeated with one change. Instead of using N$^\alpha$Boc-Ala for the 7-position residue, N$^\alpha$Boc-Val is used. Cleavage, deprotection, cyclization and purification of the peptide are carried out as in Example 1. The purified cyclic peptide has the formula (cyclo)Cys-Phe-Val-Trp-Lys-Thr-Val-Cys-OH (SEQ ID NO. 13). It is referred to as Peptide No. 12F and is selective in binding to hSSTR$_4$ as compared with its binding affinity to the other 4 receptors.

EXAMPLE 12G

The synthesis described in Example 12 is repeated with one change; instead of using N$^\alpha$Boc-Phe for the 11-position residue, N$^\alpha$Boc-Gly is used. Cleavage, deprotection, cyclization and purification are carried out as in Example 1. A purified cyclic peptide having the formula: (cyclo)H-Cys-Phe-Ala-Trp-Lys-Thr-Gly-Cys-OH (SEQ ID NO: 14) is obtained. It is referred to as Peptide 12G and is selective in binding to hSSTR$_4$ as compared with its binding affinity to the other 4 receptors.

EXAMPLE 13

The synthesis described in Example 12 is repeated with one change. Following removal of the Boc group at the N-terminal, the peptide is elongated by one residue by reaction with N$^\alpha$Boc-Tyr(2BrZ) to provide a tyrosine residue at the N-terminus. Thereafter, cleavage of the peptide from the resin and deprotection of the side chain protecting groups, followed by cyclization and purification, are carried out as in Example 1. The purified cyclic nonapeptide has the formula: (cyclo)H-Tyr-Cys-Phe-Ala-Trp-Lys-Thr-Phe-Cys-OH (SEQ ID NO:8), a purity on CZE of about 99% and is referred to as Peptide No. 13. MS analysis shows an [M+H]$^+$ mass of 1166.3 Da, which compares favorably to the calculated value of 1165.47 Da.

EXAMPLE 13A

A portion of Peptide No. 13 produced by the synthesis described in Example 13 is iodinated following purification. The purified cyclic nonapeptide is iodinated with $^{127}$I. It is referred to as Peptide No. 13A and has a purity on CZE of about 99%. MS analysis shows an [M+H]$^+$ mass of 1292.3 Da, which compares favorably to the calculated value of 1291.38 Da. This is used for the binding studies to determine selectivity. A further portion is iodinated with $^{125}$I to provide the desired radioactive ligand.

EXAMPLE 13B

The synthesis described in Example 13 is repeated with one change. Following addition of the tyrosine residue at the N-terminus, a reaction is carried out to add a carbamoyl moiety and thus create an urea group at the N-terminus using the process described in Example 3. Thereafter, cleavage of the peptide from the resin and deprotection of the side chain protecting groups, followed by cyclization and purification, are carried out as in Example 1. The purified cyclic nonapeptide has the formula: (cyclo)Cbm-Tyr-Cys-Phe-Ala-Trp-Lys-Thr-Phe-Cys-OH (SEQ ID NO:8), has a purity on CZE of about 96%, and is referred to as Peptide No. 13B. MS analysis shows an [M+H]$^+$ mass of 1209.5 Da, which compares favorably to the calculated value of 1208.49 Da.

EXAMPLE 14

The synthesis set forth in Example 13 is repeated substituting N$^\alpha$Boc-D-Trp for the 8-position residue. Cleavage, deprotection, cyclization and purification of the peptide are carried out as in Example 1. The purified cyclic peptide has the formula: (cyclo)H-Tyr-Cys-Phe-Ala-D-Trp-Lys-Thr-Phe-Cys-OH, has a purity on CZE of about 97%, and is referred to as Peptide No. 14. MS analysis shows an [M+H]$^+$ mass of 1166.4 Da, which compares favorably to the calculated value of 1165.47 Da.

EXAMPLE 15

The synthesis described in Example 6 is repeated with one change. Instead of using N$^\alpha$Boc-4-Aph(Fmoc) for the 7-position residue, N$^\alpha$Boc-4-Amp(Fmoc) is used. Cleavage, deprotection, cyclization and purification are carried out as in Example 1. A purified cyclic peptide having the formula: (cyclo)H-Tyr-Cys-Phe-4 Amp-Trp-Lys-Thr-Phe-Cys-OH (SEQ ID NO:5) is obtained which appears to be greater than 98% pure on capillary zone electrophoresis. It is referred to as Peptide 15. MS analysis shows an [M+H]$^+$ mass of 1271.6 Da which compares favorably with the calculated mass of 1270.53 Da.

EXAMPLE 15A

The synthesis described in Example 15 is repeated with one change. Following addition of the tyrosine residue at the N-terminus, a reaction is carried out to add a carbamoyl moiety and thus create an urea group at the N-terminus using the process described in Example 3. Thereafter, cleavage of the peptide from the resin and deprotection of the side chain protecting groups, followed by cyclization and purification, are carried out as in Example 1. The purified cyclic nonapeptide has the formula: (cyclo)Cbm-Tyr-Cys-Phe-Amp-Trp-Lys-Thr-Phe-Cys-OH (SEQ ID NO:5) and is referred to as Peptide No. 15A. It has a purity on CZE of about 91%. MS analysis shows an [M+H]$^+$ mass of 1314.5 Da, which compares favorably to the calculated value of 1313.55 Da.

EXAMPLE 15B

The synthesis described in Example 15 is repeated with one change. Instead of using N$^\alpha$Boc-4-Aph(Fmoc) for the 7-position residue, N$^\alpha$Boc-4-Iamp(Fmoc) is used. Cleavage, deprotection, cyclization and purification are carried out as in Example 1. A purified cyclic peptide having the formula: (cyclo)H-Tyr-Cys-Phe-4Iamp-Trp-Lys-Thr-Phe-Cys-OH (SEQ ID NO:5) is obtained which is referred to as Peptide 15B. It is selective in binding hSSTR$_4$ as compared with its binding affinity to the other 4 receptors.

EXAMPLE 16

Syntheses of Monomers

The synthesis of N$^\alpha$Boc-threo-C$^\beta$(Me,2naphthyl)D/L-alanine, which is referred to by the shorthand nomenclature as Boc-threo-D/L-C$^\beta$Me-Ala(2naphthyl) or Boc-threo-D/L-Ala(Me,2Nph) or Boc-threo-$\beta$-methyl-2naphthylalanine or Boc-threo-$\beta$-Me-2Nal, is carried out as follows:

HBr gas (39.4 g, 486 mmol) was bubbled into a solution of 2-vinylnaphthalene (75 g, 486 mmol) in benzene (100 mL) over a period of 7-8 hours at 55-60° C. The solution was cooled to room temperature, and the benzene with the small excess of HBr was removed under vacuum yielding 105 g (91%) crude of 2-(1-Bromoethyl)-naphthalene. It was used without further purification. C$_{12}$H$_{11}$Br; MS: 235.12.

2-(1-Bromoethyl)-naphthalene (105 g, 446 mmol) in anhydrous ethanol (150 mL) was added to a stirred solution of diethyl acetamidomalonate (97.6 g, 450 mmol) previously reacted with sodium ethylate (sodium metal 10.3 g, 448 mmol) in anhydrous ethanol (400 mL). The reaction mixture was stirred at 40° C. overnight. After removal of two-thirds of the solvent in vacuo and keeping the mixture in the refrigerator overnight, the precipitated product and NaBr crystals were collected by filtration. The solid was washed with cold ethanol and distilled water (to eliminate NaBr), yielding 112 g (67%) of diethyl-α-methyl-2-naphthylacetamidomalonate as white crystals: mp 148-150° C.; $C_{21}H_{25}NO_5$ MS: 371,44.

A mixture of 6N HCl/acetic acid (1:1, 1000 mL) and a mixture of erythro-(2S,3S and 2R,3R)-β-methyl-2-naphthylalanine hydrochloride and threo-(2S,3R and 2R,3S)-β-methyl-2naphthylalanine hydrochloride (230 g, 619 mmol) was refluxed for 8 hours and then evaporated to one-third of its volume. The precipitated crystals were collected by filtration, recrystallized from 200 mL of ethanol/water (1:1), and a yield of 150 g (91%) of a mixture of erythro-(2S,3S and 2R,3R)-β-methyl-2-naphthylalanine hydrochloride and threo-(2S,3R and 2R,3S)-β-methyl-2-naphthylalanine hydrochloride was obtained, mp 192-202□C (dec.). The erythro and threo isomers may be separated by fractional crystallization and differentiated by means of their NMR spectra. Quantitative determination of diastereomeric ratios may be achieved by CZE.

100 grams (377 mmol) of this mixture were dissolved in a mixture of boiling water (100 mL) and ethanol (200 mL) mixture, and the solution was allowed to crystallize overnight. Crystals were removed by filtration resulting in a product containing about 70% of erythro enantiomers, i.e. erythro-(2S,3S and 2R,3R)-β-methyl-2-naphthylalanine hydrochloride. Several recrystallizations from a 1:1 mixture of water and ethanol afforded 27 g (54%) of this racemate with a purity of greater than 95%, as determined by CZE, mp 205-213° C. (dec.) $C_{14}H_{15}NO_2$.

The mother liquors of threo-(2S,3R and 2R,3S)-β-methyl-2-naphthylalanine were concentrated to one-third of their volume, and ethanol (20 mL) was added before the pH was adjusted to 6.5 with ammonium hydroxide. The threo racemate threo-(2S,3R and 2R,3S)-β-methyl-2-naphthylalanine precipitated, but this product contained about 20% of the erythro racemate. Several recrystallizations from a 1:1 mixture of water and ethanol afforded 6.5 g (16%) of threo-(2S, 3R and 2R,3S)-β-methyl-2-naphthylalanine with a purity of greater than 95%, determined by CZE, mp 225-228° C. (dec.).

Five grams (21.8 mmol) of threo-(2R,3S and 2S,3R)-β-methyl-2-naphthylalanine were converted to $N^\alpha$-tert-butyloxycarbonyl-threo-(2R,3S and 2S,3R)-β-methyl-2-naphthylalanine (6.6 g, 92%), following literature procedures, see Dharanipragada, R., et al., *Tetrahedron Letters*, 30, 6841-6844 (1989). The oily product was converted to the DCHA salt form, to facilitate crystallization, yielding 9.2 g (82.6%) of non-separated enantiomers; mp 147-148° C., for DCHA salt $C_{19}H_{23}NO_4+C_{12}H_{23}N_1$ MS FAB:m/e 181.95, 330.10, 511.10 $(M+H)^+$, calc.: 330.17 $(M+H)^+$ 181.18 (511.35).

It is used in this racemate form for peptide syntheses which follow and is alternatively referred to as threo-D/L-Ala(Me,2Nph) or as threo-D/L-$C^\beta$Me2Nal. RP-HPLC purification can easily separate the threo-(2S,3R) isomer from the threo-(2R,3S) isomer of β-methyl-2-naphthylalanine once the SRIF peptide has been completed.

Synthesis of Analogs

The somatostatin agonist des-AA$^{1,2,4,5,12,13}$[D-Cys$^3$,Tyr$^7$, threo-D/L-$C^\beta$Me-2Nal$^8$]-SRIF having the structure: (cyclo)H-D-Cys-Phe-Tyr-threo-D/L-Ala(Me,2Nph)-Lys-Thr-Phe-Cys-OH is synthesized by the following solid phase methodology in a stepwise manner on a chloromethylated resin. The resin is composed of fine beads (20-70 microns in diameter) of a synthetic resin prepared by copolymerization of styrene with one to two percent divinylbenzene, with the benzene rings having been chloromethylated to create a reactive benzyl chloride type of precursor linker.

The addition of each of the residues of Cys, Phe, Thr and Lys is performed in accordance with Example 1.

A 3.0-equivalent excess of (Boc)-threo-(2R,3S and 2S,3R)-$C^\beta$Me-2Nal is then used. The $N^\alpha$Boc derivatives of the remaining amino acids, i.e. Tyr, Phe and D-Cys, are then sequentially coupled to produce the octapeptide intermediate: Boc-D-Cys(Mob)-Phe-Tyr(2BrZ)-threo-(2R,3S and 2S,3R)-$C^\beta$Me-2Nal-Lys(2Cl-Z)-Thr(Bzl)-Phe-Cys(Mob)-O—CH$_2$-resin support.

Cleavage of the peptide from the resin and deprotection of the side chain protecting groups are performed in hydrofluoric acid (HF) (25 ml) in the presence of 10% of anisole and 10% of dimethylsulfide for 1.5 hours at 0° C. After elimination of hydrofluoric acid under high vacuum, the resin-peptide is washed with anhydrous diethyl ether.

The resin is immediately extracted with 75% acetic acid (200 ml). The extract is filtered into a 500 milliliter round-bottom flask and is then oxidized to create the disulfide cyclic linkage by stirring vigorously while rapidly adding a 10 weight percent solution of iodine in methanol until the resultant solution remains orange-colored. It is then stirred for 40 additional minutes and quenched with 10% ascorbic acid in water until the yellow color is gone. Concentration under vacuum is carried out to remove the acetic acid, followed by dissolution in about 250 milliliters of 60% CH$_3$CN in water. The resultant solution is diluted to about 500 milliliters with distilled water, frozen and lyophilized. The synthesis results in two stereoisomers of the peptide of interest which are separable by reverse phase HPLC.

The lyophilized material is then purified by subjection to preparative RP-HPLC on a $C_{18}$ column using a linear gradient of increase of 1% B per 3 min, from the baseline % B. (Eluent A=0.25 N TEAP, pH 2.25; eluent B–60% CH$_3$CN, 40% A). Purification, in TEAP pH 2.25, is followed by subjection to rechromatography in a 0.1% TFA solution and acetonitrile on the same cartridge (gradient of 1% acetonitrile/min). The two desired cyclic stereoisomers (cyclo)H-D-Cys-Phe-Tyr-threo-(2R,3S)$C^\beta$Me-2Nal-Lys-Thr-Phe-Cys-OH and (cyclo)H-D-Cys-Phe-Tyr-threo-(2S,3R)$C^\beta$Me-2Nal-Lys-Thr-Phe-Cys-OH are obtained which each appear to be greater than 95% pure on capillary zone electrophoresis.

MS analysis shows $[M+H]^+$ masses of 1120.4 Da for both, with the calculated value being 1119.46 Da. The peptides are hereinafter referred to as Peptide Nos. 16 and 16a.

When subsequently tested for binding affinity, as described hereinafter, both were shown to have selectivity for SSTR4; however, Peptide 16A, the later-eluting isomer on RP-HPLC, was more than 100 times more selective for SSTR4 than for the closest other receptor. It has been determined to be the analog incorporating the L-threo-βMe-2Nal residue.

EXAMPLE 17

The synthesis described in Example 16 is repeated with one change. $N^\alpha$Boc-L-Cys(Mob) is used to provide the 3-position residue. Following removal of the Boc group at the N-terminus, cleavage, deprotection, cyclization and purification are carried out as in Example 1. The purified cyclic stereoisomers have the formulas: (cyclo)H-Cys-Phe-Tyr-threo-(2R,3S)$C^\beta$Me-2Nal-Lys-Thr-Phe-Cys-OH (SEQ ID NO:9) and (cyclo)H-Cys-Phe-Tyr-threo-(2S,3R)$C^\beta$Me-2Nal-Lys-Thr-Phe-Cys-OH (SEQ ID NO:9) and are referred to as Peptides Nos. 17 and 17a. They have purities on CZE of about 99%. MS analysis shows [M+H]$^+$ masses of 1120.3 Da for both, which compares favorably with the calculated value of 1119.46 Da. Both show selectivity for binding to SSTR4; however, Peptide No. 17A, the later-eluting isomer on RP-HPLC, was nearly 100 times more selective for SSTR4 than for the closest other receptor. It is determined to be the analog incorporating the L-threo-β-Me-2Nal residue.

In vitro Bioassay: The effects of the various somatostatin analogs are tested in vitro for their ability to bind to isolated cloned receptors expressed on CHO-K1 cells and CCL39 cells. CHO-K1 cells are grown in Ham's F-12 medium, and CCL39 cells are grown in Dulbecco's modified Eagle's medium/Ham's F-12(1:1) mix, supplemented with 10% fetal bovine serum, 100 U/ml penicillin and 100 μg/ml streptomycin, in humidified air containing 5% $CO_2$ at 37° C.

The molecular cloning of the genes encoding multiple somatostatin receptor subtypes permits the individual expression of these receptors in mammalian cells and the characterization of their respective pharmacological profiles. Five such receptor subtypes, termed SSTR1 through SSTR5, have been cloned and are reported and described in Raynor et al., *Molecular Pharmacology*, 43, 838-844 (1993) and in Raynor et al., *Molecular Pharmacology*, 44, 385-392 (1993). These references describe binding assays that can be used to determine whether particular SRIF analogs bind selectively to one or more of the 5 receptor types and also whether they bind to such receptor types with high or low affinity. Because these receptor types have now generally been characterized with regard to their pharmacological profiles, knowledge of the results of such binding studies, along with knowledge of the unique patterns of distribution of these receptors in the body indicate that each receptor subtype may mediate distinct but overlapping physiological effects of SRIF. As a result, compounds which bind selectively to receptors SSTR4, for example, can be used to modulate a particular physiological function of SRIF without potentially having an undesired effect resulting from another physiological function of SRIF which is mediated by other SRIF receptors.

Cells are washed twice with and scraped into ice-cold 0.05 M Tris-HCl (pH 7.4), collected by centrifugation, and homogenized using a rotor/stator/system in the same buffer. After centrifugation at 120 g for 5 min at 4° C., the supernatant is collected and centrifuged again at 48,000 g for 30 min at 4° C. The resulting pellet is resuspended in ice-cold Tris buffer, transferred into a microfuge tube, and centrifuged at 20,000 g for 15 min at 4° C. After withdrawal of the supernatant, the membrane pellet is stored at −80° C.

Receptor autoradiography is performed on 20 μm thick cryostat sections of the membrane pellets, mounted on microscope slides, and then stored at −20° C. For each of the tested compounds, complete displacement experiments are performed with the universal somatostatin ligand radioligand $^{125}$I-[Leu$^8$,D-Trp$^{22}$,Tyr$^{25}$]-somatostatin 28 that binds with strong affinity to all five receptors. Increasing concentrations of the unlabeled peptide are used ranging from 0.1-1000 nM. Unlabeled somatostatin-28 is run in parallel using the same increasing concentrations, as a control. $IC_{50}$ values are calculated after quantification of the data using a computer-assisted image processing system as known in this art. At concentrations of 100 nM, Peptide No. 1 had minimal effects on the binding of the SRIF-28 radioligand to human SSTR1 and SSTR2; it had very minimal effect upon binding to SSTR3 and SSTR5. In contrast, it selectively bound to SSTR4, displacing the binding of the radioligand to human SSTR4 with an $IC_{50}$ value of about 1.2 nM. Similarly, Peptide No. 11 containing D-Trp$^8$ and Ala$^7$ selectively binds to SSTR4 and exhibits an $IC_{50}$ of 0.98 nM, and Peptide No. 12 containing only the Ala$^7$ substitution exhibits an $IC_{50}$ of about 0.84 nM and is likewise selective. Peptide No. 8 likewise selectively binds SSTR4, and it exhibits an $IC_{50}$ of about 1.2 nM.

To confirm that an iodinated version of one of these analogs may effectively serve as a selective SSTR4 radioligand, the N-terminus-extended Tyr$^2$ analog Peptide No. 13 is synthesized, iodinated and tested for binding to the five cloned SRIF receptors. No significant binding of the iodinated Peptide No. 13A to SSTR1, 2, 3 and 5 is detectable; in contrast, the peptide still effectively binds to SSTR4, exhibiting an $IC_{50}$ of about 3.5 nM. Moreover, it is believed that its selectivity and/or affinity may be improved by acylation of the Tyr (with its phenolic hydroxyl protected) with carbamoyl, as suggested by comparison of Peptides Nos. 6 and 8. Iodination of an analog containing Tyr$^{11}$ (see Peptide Nos. 9, 10 and 10A) may also be used instead of the comparable Tyr$^2$ analog, but such is less preferred.

Screening assays, as are well known in the art which employ the receptor polypeptide SSTR4 directly from the recombinant host, can be used to identify agents useful in blocking or mimicking certain aspects of somatostatin as desired while eliminating the undesirable aspects of the hormone which may arise from activation or blocking of other receptors.

It was found from the work that was done that the 3D structures among the sstr$_4$-selective analogs had similar spatial orientation/location for some of the side chains that suggested a role for certain of these side chains in enhancing the binding affinity to the type-4 receptors as well as for disrupting binding to the other somatostatin receptors.

It was found that the characteristic elements responsible for high selectivity were the result of a close spatial arrangement of Trp$^8$, Lys$^9$ and Phe$^6$, which was a characteristic of these three side chains for sst$_4$-selective SRIF analogs. It was found that the side chains of Trp$^8$, Lys$^9$ and either Phe$^6$ or Phe$^{11}$ in all of the sst$_4$-selective analogs are almost at the same position in the binding motif and can be superimposed, as illustrated in FIG. 1 for several of the selective analogs.

FIG. 2 shows a schematic of the structural motif for the sstr$_4$-selective analogs which consists of the right spatial arrangement of the indole ring, the Lys side chain and an aromatic ring of a phenylalanine. In this pharmacophore model, the distances between the respective side chains are as follows: between Cγ of residue 8 and Cγ of Phe is 5.5-9.5 Å; Cγ of residue 8 and Cγ of Lys$^9$ is 4.5-6.5 Å; and Cγ of Phe and Cγ of Lys$^9$ is 4.5-6.4 Å. Even better selectivity appears to be obtained when the aromatic ring is in close proximity of the indole and the lysine side chains, and conservative replacements of these residues are not expected to change the binding affinities and receptor selectivity. For example, Phe can be replaced by Tyr, and D-Trp can be replaced by D-2Nal. Moreover, although the Phe is believed to contribute the side chain shown in FIG. 1, such might also be contributed by the Phe$^{11}$ in a different folding arrangement. As a result of the structural motif for the sstr$_4$-selective SRIF analogs shown in FIG. 1, this pharmacophore model for SSTR4 selective analogs was created, which permits the identity of likely candidates.

The resulting pharmacophore model can now be used in conjunction with small molecule databases such as the Available Chemical Database (ACD) to search for compounds that fit this pharmacophore pattern, which should be promising lead compounds for drug development. Methods of using pharmacophore models are described, for example, in Pharmacophore Perception, Development, and Use in Drug Design, Osman F. Guner, ed (La Jolla, Calif. 2000: International University Line).

The potencies of certain SRIF analogs to inhibit radioligand binding of $^{125}$I-[Leu$^8$,D-Trp$^{22}$,Tyr$^{24}$]SRIF-28 to the various cloned human SRIF receptors are shown in the following table wherein the IC$_{50}$ values are given in nanomolar concentration. The numbers in parentheses indicate the number of times the particular binding test was carried out.

TABLE

| Compound | IC$_{50}$ (nM) | | | | |
| --- | --- | --- | --- | --- | --- |
| | hSSTR1 | hSSTR2 | hSSTR3 | hSSTR4 | hSSTR5 |
| Peptide No. 1 | 213 ± 19 (4) | 347 ± 61 (3) | >1,000 (3) | 1.2 ± 0.1 (4) | 1,000 ± 91 (4) |
| Peptide No. 2 | 450 ± 135 (3) | 71 ± 2.1 (3) | 271 ± 120 (3) | 0.88 ± 0.3 (3) | 30 ± 7.4 (3) |
| Peptide No. 3 | 650 ± 115 (3) | >1,000 (3) | 780 ± 62 (3) | 1.46 ± 0.07 (3) | >1,000 (3) |
| Peptide No. 4 | 840 ± 101 (4) | 120 ± 15 (3) | 650 ± 161 (3) | 1.1 ± 0.2 (3) | 103 ± 15 (3) |
| Peptide No. 5 | ~1,100 | >1,000 | 630 | 2.9 | 610 |
| Peptide No. 6 | 270 ± 39 (4) | 260 ± 20 (3) | 135 ± 25 (4) | 1.9 ± 0.3 (4) | 663 ± 157 (4) |
| Peptide No. 7 | 517 ± 159 (3) | 56 ± 5.8 (3) | 263 ± 97 (3) | 1.2 ± 0.3 (3) | 34 ± 8.6 (3) |
| Peptide No. 8 | 347 ± 120 (3) | 550 ± 276 (3) | 210 ± 36 (3) | 1.2 ± 0.3 (3) | 317 ± 92 (3) |
| Peptide No. 9 | 327 ± 37 (3) | 170 ± 25 (3) | 247 ± 86 (3) | 1.1 ± 0.2 (3) | 240 ± 45 (3) |
| Peptide No. 10 | 757 ± 94 (3) | >1000 (3) | 587 ± 150 (3) | 3 ± 0.4 (3) | 557 ± 70 (3) |
| Peptide No. 10A | >1,000 (3) | 227 ± 108 (3) | 623 ± 340 (3) | 4.3 ± 2.4 (3) | 110 ± 12 (3) |
| Peptide No. 11 | >1,000 (3) | 183 ± 18 (3) | 897 ± 103 (3) | 0.98 ± 0.1 (4) | 199 ± 56 (4) |
| Peptide No. 12 | >1000 (3) | 807 ± 146 (3) | 750 ± 278 (3) | 0.84 ± 0.2 (3) | 633 ± 186 (3) |
| Peptide No. 12A | >10,000 (2) | >1000 (2) | >1000 (2) | 3.5 ± 0.8 (2) | >1000 (2) |
| Peptide No. 12B | >10,000 (2) | >1000 (2) | >1000 (2) | 9.5 ± 2.5 (2) | >1000 (2) |
| Peptide No. 13 | >1000 (4) | 622 ± 85 (4) | 621 ± 213 (4) | 1.98 ± 0.45 (4) | 692 ± 166 (4) |
| Peptide No. 13A | >1000 (2) | >1000 (2) | 1025 ± 475 (2) | 3.5 ± 0.8 (4) | >1000 ( |
| Peptide No. 13B | >1000 (3) | 700 ± 92 (3) | 980 ± 73 (3) | 2.36 ± 0.47 (3) | >1000 (3) |
| Peptide No. 14 | 330 ± 12 (3) | 57 ± 17 (3) | 347 ± 120 (3) | 1.1 ± 0.2 (3) | 51 ± 20 (3) |
| Peptide No. 15 | >1000 (2) | 259 ± 9 (2) | 326 ± 7 (2) | 2.4 ± 0.2 (3) | 342 ± 82 (2) |
| Peptide No. 15A | >1000 ± 50 (3) | 118 ± 42 (3) | 197 ± 48 (3) | 3.2 ± 0.6 (3) | 247 ± 27 (3) |
| Peptide No. 16 | 545 ± 122 (4) | 12 ± 2 (4) | 14 ± 3 (4) | 0.55 ± 0.03 (4) | 27 ± 5.6 (3) |
| Peptide No. 16A | >10,000 (6) | 339 ± 103 (5) | 664 ± 81 (5) | 3.5 ± 0.5 (6) | 668 ± 86 (6) |
| Peptide No. 17 | 410 ± 110 (2) | 30 ± 0 (2) | 18 ± 4 (2) | 2.3 ± 1.7 (2) | 18 ± 0.5 (2) |
| Peptide No. 17A | >1,000 (5) | 194 ± 68 (5) | 825 ± 288 (4) | 2.8 ± 0.8 (5) | 360 ± 213 (4) |

The peptides of the invention not only provide more selective ligands for binding SSTR4, but the use of labeled peptides, for example, a radioiodinated analog Peptide No. 13A, facilitates drug screening for even more effective antagonists. Competitive binding assays with candidate compounds would first be carried out in this manner with SSTR4 to search for high binding affinity; then by screening the multiple SRIF receptors, it could be confirmed whether there was selective binding to only this receptor, as is desired. The non-radiolabeled peptides of the invention may be used to treat diseases of all organs known to express SSTR4, including the lung, gastrointestinal tract and kidneys.

Because, as shown above, additions to the N-terminus of the SRIF analog do not appear to adversely affect the selective binding, it should be clear that these compounds can be complexed with a cytotoxic or a radioactive agent for the purpose of carrying that agent to a tumor or other tissue for which degradation is desired. For example, a dialdehyde linker such as glutaraldehyde may be used to link the SRIF analog to saporin or gelonin. Likewise, linkers such as DOTA or DTPA or other suitable chelating agents can be used to complex the SRIF analog with a highly radioactive element as indicated hereinbefore. Examples of suitable chelating groups for chelating a radioactive metal atom are tetradentate chelating agents or groups derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N',N'',N'''-tetra-acetic acid (DOTA), hydroxyethyldiamine triacetic acid (HEDTA), 1,4,8,11-tetra-azacyclo-tetradecane-N,N',N'',N'''-tetra-acetic acid (TETA), substituted DTPA, substituted EDTA. Other chelators are disclosed in WO 95/22341. Preferred chelators are derived from EDTA and DOTA. Suitable salts are $^{111}$In-oxinte, $^{99m}$Tc-tartrate which can generally be formed in a simple manner under conditions that are not detrimental to the peptide.

If desired, the solubility of the SRIF analogs can be improved by acylation of the N-terminal amino group using a hydrophilic compound, such as hydroorotic acid or the like, or by reaction with a suitable isocyanate, such as methylisocyanate or isopropylisocyanate, to create a urea moiety at the N-terminus. Such substitutions onto an aminophenylalanine residue are also considered suitable for producing residues similar to Tyr that would be equivalents therefor in the 2- or 7-position. Other agents can also be N-terminally linked that will increase the duration of action of the SRIF analog as known in this art.

These SRIF analogs or nontoxic salts thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. Such a pharmaceutical composition to be used for detecting malignant human tumors, including the metastasis thereof, in tissues may include, in addition to a pharmaceutically acceptable carrier material, and an optional pharmaceutically acceptable adjuvant, a labeled peptide as the active substance, in a quantity sufficient for external imaging, for detection by a gamma-detecting probe or for combating or controlling tumors. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician to combat specific tumors and cancers or to mediate other conditions where the SSTR4 receptors exert a control function, such as coupling to a tyrosine phosphatase so that stimulation of this enzyme can be carried out to mediate the anti-proliferative effects of SRIF. The required dosage will vary with the particular condition being treated, with the severity of the condition and with the duration of desired treatment.

Such peptides are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like.

It may also be desirable to deliver these SRIF analogs over prolonged periods of time, for example, for periods of one week to one year from a single administration, and slow release, depot or implant dosage forms may be utilized as well known in this art. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain an SRIF analog or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptides should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of an SRIF analog that, when administered peripherally, e.g. intravenously, in a physiologically acceptable composition, is sufficient to achieve a plasma concentration thereof from about 0.1 µg/ml to about 100 µg/ml, preferably from about 1 µg/ml to about 50 µg/ml, more preferably at least about 2 µg/ml and usually 5 to 10 µg/ml. In these amounts, they may be used to desirably affect gastric secretion.

When the composition is to be used for imaging or therapeutic treatments, poor shelf life of the radiolabelled compound and/or the short half-life of the radionuclide may require that the user carry out the labeling reaction with the radionuclide in the clinical hospital or laboratory. In such instances, the various reaction ingredients may be provided to the user in the form of a so-called "kit". The manipulations necessary to perform the desired reaction should be as simple as possible to enable the user to prepare the radioactive labeled composition from the kit using facilities that normally be at one's disposal. Accordingly, a kit for preparing a radiopharmaceutical composition, for detecting and localizing malignant tumors and their metastases in tissues might comprise (i) an SSTR4 selective peptide, an inert pharmaceutically acceptable carrier and/or formulating agent with optional adjuvants, (ii) a solution of a salt or chelate of a radioactive metal isotope, and (iii) instructions for use with a prescription for reacting the ingredients present in the kit.

Preferably, the peptide to be used as an ingredient of such a kit has been derivatized by a reaction with a chelating agent as defined hereinbefore. The resulting peptide conjugate provides a facility for firmly attaching the radionuclide in a simple manner. Suitable chelating agents for modifying the peptide are described in detail hereinbefore. N-containing di- or polyacetic acids or their derivatives, such as the compounds mentioned before, have proved to be pre-eminently suitable for attaching various metal radionuclides, such as $^{111}$In and $^{113m}$In, to the peptide molecules. The kit to be supplied to the user may also comprise the other ingredients defined above, together with instructions for use, whereas the solution of a salt or chelate of the radionuclide having a limited shelf life, may be supplied to the user separately.

For example, a kit to prepare a radiopharmaceutical composition labeled with Tc-99m, Re-186 or Re-188 may comprise, in addition to the ingredients defined in (i) and (ii) above, a reducing agent and, if desired, a chelator, and (iii) instructions for use, with a prescription for reacting the ingredients of the kit with Tc-99m in the form of a pertechnetate solution, or with Re-186 or Re-188 in the form of a perrhenate solution. If desired, various ingredients of the kit may be combined, provided they are compatible. The kit should comprise a reducing agent to reduce the pertechnetate or perrhenate, for example, a dithionite, a metallic reducing agent or a complex-stabilizing reducing agent, e.g. $SnCl_2$, Sn(II)-tartrate, Sn(II)-phosphonate or -pyro-phosphate, or Sn(II)-glucoheptonate. The pertechnetate or perrhenate solution can simply be obtained from a suitable vendor. When the radionuclide is present in the kit itself, the complex-forming reaction with the peptide can simply be produced by combining the components in a neutral medium and causing them to react. For that purpose the radionuclide may be reacted with the peptide in the form of a chelate bound to a comparatively weak chelator, as described hereinbefore.

When the kit comprises a derivatized peptide as defined hereinbefore and is intended for the preparation of a radiopharmaceutical composition, labeled with Tc-99m, Re-186 or Re-188, the radionuclide will preferably be added separately in the form of a pertechnetate or perrhenate solution. In that case the kit will comprise a suitable reducing agent and, if desired, a chelator, the former to reduce the pertechnetate or the perrhenate. As a reducing agent may be used, for example, a dithionite or a metallic reducing agent. The ingredients may optionally be combined, provided they are compatible. Such a monocomponent kit, in which the combined ingredients are preferably lyophilized, is excellently suitable for being reacted, by the user, with the radionuclide solution. A metallic reducing agent, for example, Sn(II), Ce(III), Fe(II), Cu(I), Ti(III) or Sb(III); Sn(II), may be used. The peptide constituent of the above-mentioned kits may be supplied as a solution, for example, in the form of a physiological saline solution, or in some buffer solution, but it is preferably present in a dry condition, for example, in the lyophilized condition. When used as a component for an injection liquid it should be sterile, in which, when the constituent is in the dry state, the user should preferably use a sterile physiological saline solution as a solvent. If desired, the above-mentioned constituent may be stabilized in the conventional manner with suitable stabilizers, for example, ascorbic acid, gentisic acid or salts of these acids.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. Although the claims variously define the invention in terms of a peptide sequence, it should be understood that such is intended to include nontoxic salts thereof which are well known to be the full equivalent thereof and which are most frequently administered. Instead of the simple free acid at the C-terminus, a lower alkyl ester or amide may be incorporated as well known in the peptide art. Cyclic peptides having an amino acid residue sequence substantially identical to the sequence of the SRIF analogs specifically shown herein, in which one or more residues have been conservatively substituted with a functionally similar amino acid residue, are also considered to be equivalents so long as they selectively bind to SSTR4.

As previously indicated, these specified modifications can be incorporated in previously disclosed SRIF analogs to create SSTR4-selectivity. Although not preferred, one or two of the deleted residues in the ring portion may be included; for example, incorporation of a residue, such as Asn, in the 5-position is considered optional. Likewise, inclusion of residues in the 1- and 2-position is optional, but except for Tyr, D-Tyr, D-Ala or an acyl group, such elongation is not considered worthwhile. Broadly it is felt that a preferred group of cyclic somatostatin analog peptides can be created having specific affinity for the SRIF receptor SSTR4 by modifying the amino acid sequence of existing SRIF analogs which are known in the art to exhibit SRIF biological activity. Such a modified peptide should have an amino acid sequence at least 8 residues in length, contain a Cys-Cys disulfide bond with a sequence of at least 6 residues located between such Cys residues as a part of a ring structure, and contain Phe-$Xaa_7$-$Xaa_8$-Lys-Thr-$Xaa_{11}$ (SEQ ID NO:10) or its equivalent generally adjacent the N-terminal Cys of such ring structure; these SRIF analog peptides are characterized by $Xaa_7$ being Aph, Amp or Ala, with $Xaa_8$ being substituted or unsubstituted Trp, 2Nal or D-Trp, preferably Trp, and by $Xaa_{11}$ preferably being Phe, Ala or Tyr. By equivalent is meant a functionally similar pentapeptide, where one or more residues have been substituted by making a conservative substitution, as described in detail in U.S. Pat. No. 6,214,797. Such peptides and salts thereof are considered as being within the scope of the claimed invention.

The disclosures of all patents, published patent applications and publications set forth hereinbefore are expressly incorporated herein by reference. As used herein, all temperatures are ° C. and all ratios are by volume. Percentages of liquid materials are also by volume.

Various features of the invention are emphasized in the claims which follow.

The invention claimed is:

1. A cyclic somatostatin(SRIF) analog peptide which selectively binds the SRIF receptor SSTR4 in contrast to its affinity for SSTR1, SSTR2, SSTR3 and SSTR5, which peptide comprises the amino acid sequence (cyclo)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2) wherein $Xaa_1$ is des-Xaa, D-Ala, Ala, L-Hor, Cbm, an acyl group having up to 20 carbon atoms or alkyl($C_1$ to $C_6$);

$Xaa_2$ is Tyr, D-Tyr, Gly or des-Xaa;

$Xaa_3$ is Cys or D-Cys;

$Xaa_4$ is des-Xaa;

$Xaa_5$ is des-Xaa;

$Xaa_7$ is an amino acid selected from the group consisting of Ala, Aph, Amp, Iamp, and Val;

$Xaa_8$ is an amino acid selected from the group consisting of (A)Trp, (A)D-Trp, and 2Nal, wherein A is H, Cl, F, Br, Me, $NO_3$, OMe or formyl;

$Xaa_{11}$ is Ala, Gly, Val, Phe or Tyr;

$Xaa_{12}$ is des-Xaa; and
$Xaa_{13}$ is des-Xaa.

2. The peptide according to claim 1 wherein $Xaa_1$ and $Xaa_2$, are des-Xaa.

3. The peptide according to claim 1 wherein
   $Xaa_1$ is Cbm;
   $Xaa_2$ is des-Xaa;
   $Xaa_7$ is Aph;
   $Xaa_8$ is Trp; and
   $Xaa_{11}$ is Phe.

4. The peptide according to claim 1 comprising the amino acid sequence: (cyclo)$Xaa_1$-Tyr-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2), where
   $Xaa_1$ is Acyl, Cbm or des-Xaa;
   $Xaa_3$ is Cys or D-Cys;
   $Xaa_7$ is Ala, Aph, Amp or Iamp;
   $Xaa_8$ is Trp, D-Trp or 2Nal;
   $Xaa_{11}$ is Ala, Phe or Tyr; and
   $Xaa_4$, $Xaa_5$, $Xaa_{12}$ and $Xaa_{13}$ are des-Xaa.

5. A cyclic somatostatin(SRIF) analog peptide having specific affinity for the SRIF receptor SSTR4 in contrast to its affinity for SSTR1, SSTR2, SSTR3 and SSTR5, which peptide has an amino acid sequence (cyclo)$Xaa_1$-$Xaa_2$-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2), where
   $Xaa_1$ is Ac, Cbm or des-Xaa;
   $Xaa_2$ is Tyr, D-Tyr or des-Xaa;
   $Xaa_3$ is Cys or D-Cys;
   $Xaa_7$ is Ala, Aph, Amp or Iamp;
   $Xaa_8$ is Trp, D-Trp or 2Nal,
   $Xaa_{11}$ is Phe or Tyr; and
   $Xaa_4$, $Xaa_5$, $Xaa_{12}$ and $Xaa_{13}$ are des-Xaa.

6. A cyclic somatostatin(SRIF) analog peptide having specific affinity for the SRIF receptor SSTR4 in contrast to its affinity for SSTR1, SSTR2, SSTR3 and SSTR5, which peptide has an amino acid sequence (cyclo)$Xaa_1$-Tyr-$Xaa_3$-$Xaa_4$-$Xaa_5$-Phe-$Xaa_7$-$Xaa_8$-Lys-Thr-$Xaa_{11}$-$Xaa_{12}$-$Xaa_{13}$-Cys (SEQ ID NO:2), where
   $Xaa_1$ is Ac, Cbm or des-Xaa;
   $Xaa_3$ is Cys;
   $Xaa_7$ is Ala, Aph or Amp;
   $Xaa_8$ is Trp, D-Trp or 2Nal
   $Xaa_{11}$ is Phe or Tyr; and
   $Xaa_4$, $Xaa_5$, $Xaa_{12}$ and $Xaa_{13}$ are des-Xaa.

7. The peptide according to claim 6 wherein $Xaa_7$ is Ala and $Xaa_8$ is Trp or 2Nal.

8. A peptide comprising the amino acid sequence: Tyr-Cys-Phe-Ala-Trp-Lys-Thr-Phe-Cys (SEQ ID NO:8).

9. The peptide according to claim 8 wherein Tyr is radioactively iodinated.

10. The peptide according to claim 6 wherein $Xaa_7$ is Aph.

11. The peptide according to claim 6 wherein $Xaa_7$ is Amp.

12. The peptide according to claim 5 wherein $Xaa_7$ is Ala, Aph or Amp.

13. The peptide according to claim 12 wherein $Xaa_7$ is Ala and $Xaa_{11}$ is Ala.

14. The peptide according to claim 8 wherein there is also present at the N-terminus a complexing agent or a conjugating agent.

15. The peptide according to claim 8 wherein a complexing agent is present at the N-terminus which is capable of joining to a radioactive nuclide.

16. The peptide according to claim 8 wherein a conjugating agent is present at the N-terminus which is capable of linking to a cytotoxin.

17. A pharmaceutical composition comprising a mixture of the peptide according to claim 6 and at least one pharmaceutically acceptable carrier.

18. A method for destroying SSTR4-containing cells, which method comprises administering an amount of the peptide to the cell according to claim 14 which includes a radioactive nuclide or a cytotoxin, which amount is effective to destroy such cells.

19. A method of detecting, in the body of a human being, tumors having SSTR4 and their metastases in tissues, which in healthy condition and in non-neoplastic conditions of chronic inflammation do not contain substantial quantities of SSTR4, which method comprises
   (i) administering to said human, in a quantity sufficient for external imaging, a composition comprising a peptide according to claim 8, said peptide being labeled with (a) a radioactive metal isotope or (b) a paramagnetic metal atom or (c) a radioactive halogen isotope, and thereupon
   (ii) subjecting said human to external imaging, by radioactive scanning or by magnetic resonance imaging, to determine the targeted sites in the body thereof in relation to the background activity, in order to allow detection and localization of said tumors in the body.

20. A method for screening for ligands that bind with high affinity to SSTR4, which method comprises
   carrying out a competitive binding assay with (1) SSTR4, (2) the peptide according to claim 6 which is labeled and (3) a candidate ligand, and
   determining the ability of the said candidate ligand to displace said labeled peptide.

* * * * *

UNITED STATES PATENT AND TRADEMARK OFFICE
CERTIFICATE OF CORRECTION

| | | |
|---|---|---|
| PATENT NO. | : 7,238,775 B2 | Page 1 of 1 |
| APPLICATION NO. | : 11/041676 | |
| DATED | : July 3, 2007 | |
| INVENTOR(S) | : Jean E.F. Rivier et al. | |

It is certified that error appears in the above-identified patent and that said Letters Patent is hereby corrected as shown below:

On the title page item (56), OTHER PUBLICATIONS, line 5, change "Jiange" to --Jiang--;

and Column 34, lines 8-9, delete "also present" and substitute --coupled--.

Signed and Sealed this

Twenty-eighth Day of August, 2007

JON W. DUDAS
*Director of the United States Patent and Trademark Office*

SEQUENCE LISTING

<160> NUMBER OF SEQ ID NOS: 14

<210> SEQ ID NO 1
<211> LENGTH: 14
<212> TYPE: PRT
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: X = D-Ala, Ala, L-Hor or deleted
<220> FEATURE:
<221> NAME/KEY: misc_feature
<222> LOCATION: (2)..(2)
<223> OTHER INFORMATION: X =  Tyr, D-Tyr, Gly or deleted
<220> FEATURE:
<221> NAME/KEY: misc_feature
<222> LOCATION: (3)..(3)
<223> OTHER INFORMATION: X = Cys or D-Cys
<220> FEATURE:
<221> NAME/KEY: misc_feature
<222> LOCATION: (4)..(4)
<223> OTHER INFORMATION: X = Lys or deleted

```
<220> FEATURE:
<221> NAME/KEY: misc_feature
<222> LOCATION: (5)..(5)
<223> OTHER INFORMATION: X = Asn or deleted
<220> FEATURE:
<221> NAME/KEY: misc_feature
<222> LOCATION: (7)..(7)
<223> OTHER INFORMATION: X = Ala, Aph, Amp, Iamp, Val or Tyr
<220> FEATURE:
<221> NAME/KEY: misc_feature
<222> LOCATION: (8)..(8)
<223> OTHER INFORMATION: X = Trp, D-Trp, Nal or threo-L-CbetaMe-2Nal
<220> FEATURE:
<221> NAME/KEY: misc_feature
<222> LOCATION: (11)..(11)
<223> OTHER INFORMATION: X = Ala, Gly, Val, Phe or Tyr
<220> FEATURE:
<221> NAME/KEY: misc_feature
<222> LOCATION: (12)..(12)
<223> OTHER INFORMATION: X = Thr or deleted
<220> FEATURE:
<221> NAME/KEY: misc_feature
<222> LOCATION: (13)..(13)
<223> OTHER INFORMATION: X = Ser, D-Ser or deleted

<400> SEQUENCE: 2

Xaa Xaa Xaa Xaa Xaa Phe Xaa Xaa Lys Thr Xaa Xaa Xaa Cys
1               5                   10

<210> SEQ ID NO 3
<211> LENGTH: 8
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: X = Aph, Amp or Iamp

<400> SEQUENCE: 3

Cys Phe Xaa Trp Lys Thr Phe Cys
1               5

<210> SEQ ID NO 4
<211> LENGTH: 8
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: X = Aph, Amp or Iamp
<220> FEATURE:
<221> NAME/KEY: misc_feature
<222> LOCATION: (4)..(4)
<223> OTHER INFORMATION: X = Trp, D-Trp or Nal

<400> SEQUENCE: 4

Cys Phe Xaa Xaa Lys Thr Phe Cys
1               5

<210> SEQ ID NO 5
<211> LENGTH: 9
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: X = Aph, Amp or Iamp
```

```
<400> SEQUENCE: 5

Tyr Cys Phe Xaa Trp Lys Thr Phe Cys
1               5

<210> SEQ ID NO 6
<211> LENGTH: 8
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: X = Aph, Amp or Iamp

<400> SEQUENCE: 6

Cys Phe Xaa Trp Lys Thr Tyr Cys
1               5

<210> SEQ ID NO 7
<211> LENGTH: 8
<212> TYPE: PRT
<213> ORGANISM: Artificial
<220> FEATURE:
<223> OTHER INFORMATION: Synthetic Peptide

<400> SEQUENCE: 7

Cys Phe Ala Trp Lys Thr Phe Cys
1               5

<210> SEQ ID NO 8
<211> LENGTH: 9
<212> TYPE: PRT
<213> ORGANISM: Artificial
<220> FEATURE:
<223> OTHER INFORMATION: Synthetic Peptide

<400> SEQUENCE: 8

Tyr Cys Phe Ala Trp Lys Thr Phe Cys
1               5

<210> SEQ ID NO 9
<211> LENGTH: 8
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: X = threo-(2R,3S)CbetaMe-2Nal- or
      threo-(2S,3R)CbetaMe-2Nal-

<400> SEQUENCE: 9

Cys Phe Tyr Xaa Lys Thr Phe Cys
1               5

<210> SEQ ID NO 10
<211> LENGTH: 6
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: X = Ala, Aph, Amp or Iamp
<220> FEATURE:
```

```
<221> NAME/KEY: misc_feature
<222> LOCATION: (3)..(3)
<223> OTHER INFORMATION: X = Trp, D-Trp or Nal
<220> FEATURE:
<221> NAME/KEY: misc_feature
<222> LOCATION: (6)..(6)
<223> OTHER INFORMATION: X = Ala, Phe or Tyr

<400> SEQUENCE: 10

Phe Xaa Xaa Lys Thr Xaa
1               5

<210> SEQ ID NO 11
<211> LENGTH: 8
<212> TYPE: PRT
<213> ORGANISM: Artificial
<220> FEATURE:
<223> OTHER INFORMATION: Synthetic Peptide

<400> SEQUENCE: 11

Cys Phe Ala Trp Lys Thr Ala Cys
1               5

<210> SEQ ID NO 12
<211> LENGTH: 8
<212> TYPE: PRT
<213> ORGANISM: Artificial
<220> FEATURE:
<223> OTHER INFORMATION: Synthetic Peptide

<400> SEQUENCE: 12

Cys Phe Ala Trp Lys Thr Val Cys
1               5

<210> SEQ ID NO 13
<211> LENGTH: 8
<212> TYPE: PRT
<213> ORGANISM: Artificial
<220> FEATURE:
<223> OTHER INFORMATION: Synthetic Peptide

<400> SEQUENCE: 13

Cys Phe Val Trp Lys Thr Val Cys
1               5

<210> SEQ ID NO 14
<211> LENGTH: 8
<212> TYPE: PRT
<213> ORGANISM: Artificial
<220> FEATURE:
<223> OTHER INFORMATION: Synthetic Peptide

<400> SEQUENCE: 14

Cys Phe Ala Trp Lys Thr Gly Cys
1               5
```